US010478631B2

(12) United States Patent
Chapman et al.

(10) Patent No.: US 10,478,631 B2
(45) Date of Patent: Nov. 19, 2019

(54) WEARABLE CARDIOVERTER DEFIBRILLATOR (WCD) SYSTEM USING SENSOR MODULES WITH REASSURANCE CODE FOR CONFIRMATION BEFORE SHOCK

(71) Applicant: West Affum Holdings Corp., Grand Cayman (KY)

(72) Inventors: Fred William Chapman, Newcastle, WA (US); Gregory T. Kavounas, Bellevue, WA (US)

(73) Assignee: West Affum Holdings Corp., Grand Cayman (KY)

( * ) Notice: Subject to any disclaimer, the term of this patent is extended or adjusted under 35 U.S.C. 154(b) by 0 days.

(21) Appl. No.: 15/905,575

(22) Filed: Feb. 26, 2018

(65) Prior Publication Data
US 2018/0289976 A1 Oct. 11, 2018

Related U.S. Application Data

(63) Continuation of application No. 14/855,106, filed on Sep. 15, 2015, now Pat. No. 9,901,741.
(Continued)

(51) Int. Cl.
*A61N 1/00* (2006.01)
*A61N 1/39* (2006.01)
(Continued)

(52) U.S. Cl.
CPC .......... *A61N 1/3987* (2013.01); *A61B 5/0059* (2013.01); *A61B 5/0402* (2013.01);
(Continued)

(58) Field of Classification Search
CPC .... A61N 1/3987; A61N 1/046; A61N 1/3968; A61B 5/0059; A61B 5/0402;
(Continued)

(56) References Cited

U.S. PATENT DOCUMENTS 3,724,355 A 4/1973 Unger
4,583,524 A 4/1986 Hutchins
(Continued)

FOREIGN PATENT DOCUMENTS

WO 1998/039061 A2 9/1998
WO 2004/091719 A2 10/2004

OTHER PUBLICATIONS

Heartstart MRx and XL AED Algorithm—Application Nole, Jul. 2001, Edition 2 Philips Healthcare, USA.
(Continued)

*Primary Examiner* — Lindsey G Wehrheim
(74) *Attorney, Agent, or Firm* — Jennifer Junkin; John Whitaker

(57) ABSTRACT

A wearable cardioverter defibrillator ("WCD") system includes a support structure that can be worn by a patient, and a defibrillator coupled to the support structure. An ECG input, rendered from an ECG of the patient, may meet a primary shock criterion. One or more sensor modules are further provided, which are worn by the patient at different times. The sensor modules may monitor different physiological parameters of the patient, and transmit signals about them. The WCD system further has a multi-sensor interface to receive the transmitted signals, and a processor to determine from them whether a secondary shock criterion is met. If both the primary and the secondary shock criteria are met, the decision is to shock. The signals increase specificity of the detection, while the patient can wear different modules depending on context.

30 Claims, 15 Drawing Sheets

SAMPLE COMPONENTS OF WEARABLE
CARDIOVERTER DEFIBRILLATOR (WCD)
SYSTEM

Related U.S. Application Data

(60) Provisional application No. 62/159,764, filed on May 11, 2015.

(51) Int. Cl.

| | | |
|---|---|---|
| *A61B 5/0402* | (2006.01) | |
| *A61B 5/00* | (2006.01) | |
| *A61B 5/103* | (2006.01) | |
| *A61B 8/08* | (2006.01) | |
| *A61N 1/04* | (2006.01) | |
| *A61B 8/00* | (2006.01) | |
| *A61B 5/0205* | (2006.01) | |
| *A61B 5/021* | (2006.01) | |
| *A61B 5/024* | (2006.01) | |
| *A61B 5/026* | (2006.01) | |
| *A61B 5/11* | (2006.01) | |

(52) U.S. Cl.
CPC .......... *A61B 5/1032* (2013.01); *A61B 5/4836* (2013.01); *A61B 8/0883* (2013.01); *A61B 8/4427* (2013.01); *A61B 8/488* (2013.01); *A61N 1/046* (2013.01); *A61N 1/3968* (2013.01); *A61B 5/0024* (2013.01); *A61B 5/021* (2013.01); *A61B 5/024* (2013.01); *A61B 5/0205* (2013.01); *A61B 5/026* (2013.01); *A61B 5/11* (2013.01)

(58) Field of Classification Search
CPC ... A61B 5/1032; A61B 5/4836; A61B 8/0883; A61B 8/4427; A61B 8/488; A61B 5/0024; A61B 5/0205; A61B 5/021; A61B 5/024; A61B 5/026; A61B 5/11
See application file for complete search history.

(56) References Cited

U.S. PATENT DOCUMENTS

| | | |
|---|---|---|
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,353,793 A | 10/1994 | Bomn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,437,083 B1 | 7/2002 | Owen et al. |
| 6,529,875 B1 | 3/2003 | Nakajima |
| 6,546,285 B1 | 4/2003 | Owen et al. |
| 6,681,003 B2 | 1/2004 | Linder et al. |
| 6,762,917 B1 | 7/2004 | Verblest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,140,154 B2 | 10/2012 | Donnelly et al. |
| 8,369,944 B2 | 2/2013 | Macho et al. |
| 8,644,925 B2 | 2/2014 | Volpe et al. |
| 8,838,235 B2 | 9/2014 | Cowan et al. |
| 8,897,860 B2 | 11/2014 | Volpe et al. |
| 8,965,500 B2 | 2/2015 | Macho et al. |
| 9,008,801 B2 | 4/2015 | Kaib et al. |
| 9,131,901 B2 | 9/2015 | Volpe et al. |
| 9,132,267 B2 | 9/2015 | Kalb |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0312709 A1 | 12/2008 | Volpe et al. |
| 2009/0005827 A1 | 1/2009 | Weintraub et al. |
| 2010/0007413 A1 | 1/2010 | Heleikson |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0197353 A1 | 8/2012 | Donnelly et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0085081 A1 | 3/2014 | Brown et al. |
| 2014/0163334 A1 | 6/2014 | Volpe et al. |
| 2014/0296931 A1 | 10/2014 | Chapman et al. |
| 2014/0303680 A1 | 10/2014 | Donnelly et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2016/0004831 A1 | 1/2016 | Carlson et al. |
| 2017/0056682 A1* | 3/2017 | Kumar ................. A61N 1/3968 |

OTHER PUBLICATIONS

The LifeVest Network/Patient Data Management System, Zoll, 2015, 2000503 Rev A.

Klein, H.U., et al., "Risk Stratification for Implantable Cardioverter Defibrillator Therapy: The Role of the Wearable Cardioverter-Defibrillator," Clinical update, European Heart Journal, May 31, 2013, pp. 1-14, doi:10.1093/eurheartjeht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Dosinas, Vaitkunas, Daunoras, "Measurement of Human Physiological Parameters in the Systems of Active Clothing and Wearable Technologies," Electronics and Electrical Engineering, 2006, pp. 77-82, Nr. 7(71), ISSN 1392-1215.

Fingertip Pulse Oximeter MQ3000 User Manual Ver1.0C11, Mar. 2, 2012, 2 pages, AIRIAL.

* cited by examiner

*SAMPLE COMPONENTS OF WEARABLE CARDIOVERTER DEFIBRILLATOR (WCD) SYSTEM*

*PATTERN OF WEARING*

FIG. 4   METHODS

| SCENARIO | S1 ASSU-RANCE? | S2 ASSU-RANCE? | S3 ASSU-RANCE? | SECONDARY SHOCK CRITERION MET? |
|---|---|---|---|---|
| 1 | YES | YES | YES | NO |
| 2 | NO | [ANY] | [ANY] | YES |
| 3 | [ANY] | NO | [ANY] | YES |
| 4 | [ANY] | [ANY] | NO | YES |

660

FIG. 6     *TABLE*

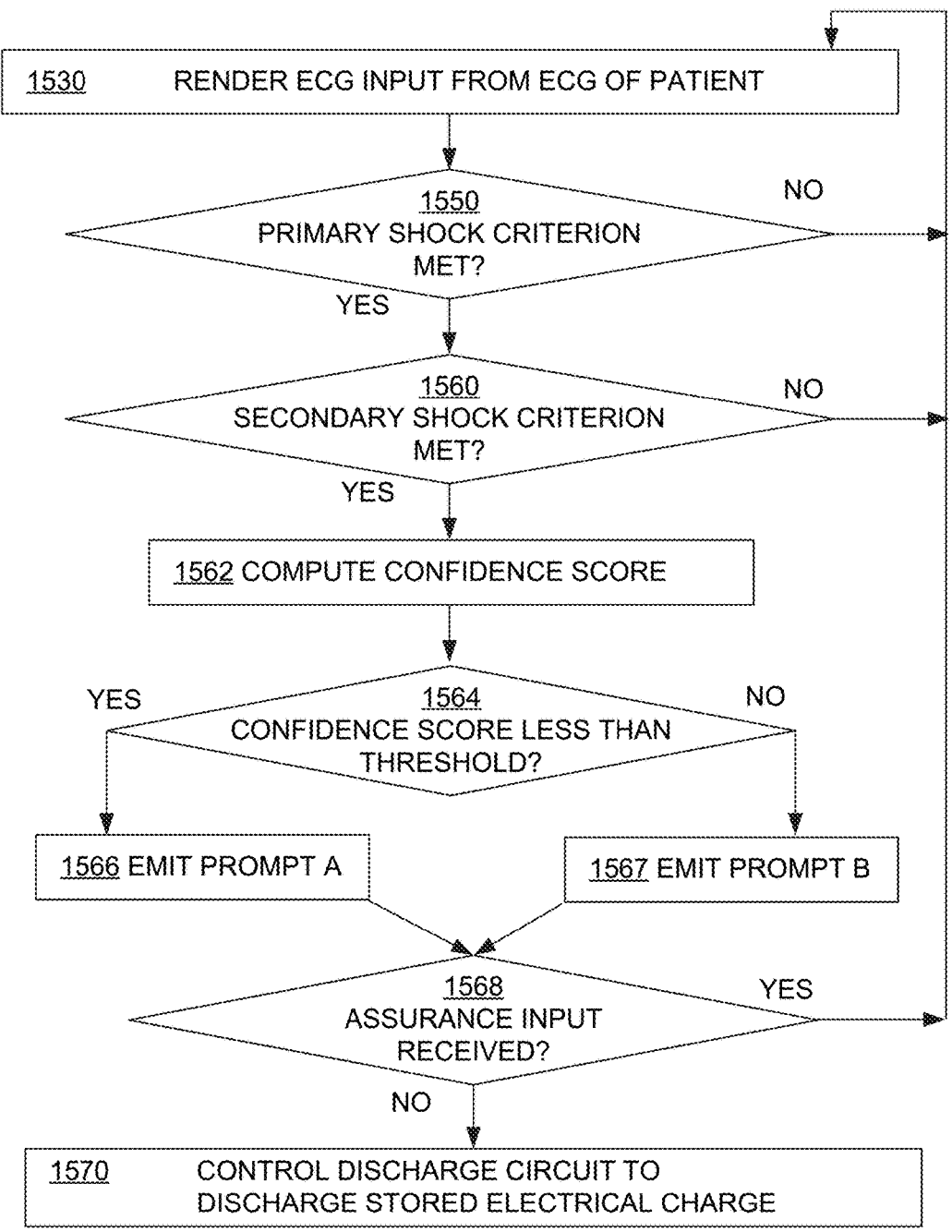
FIG. 15  *METHODS*

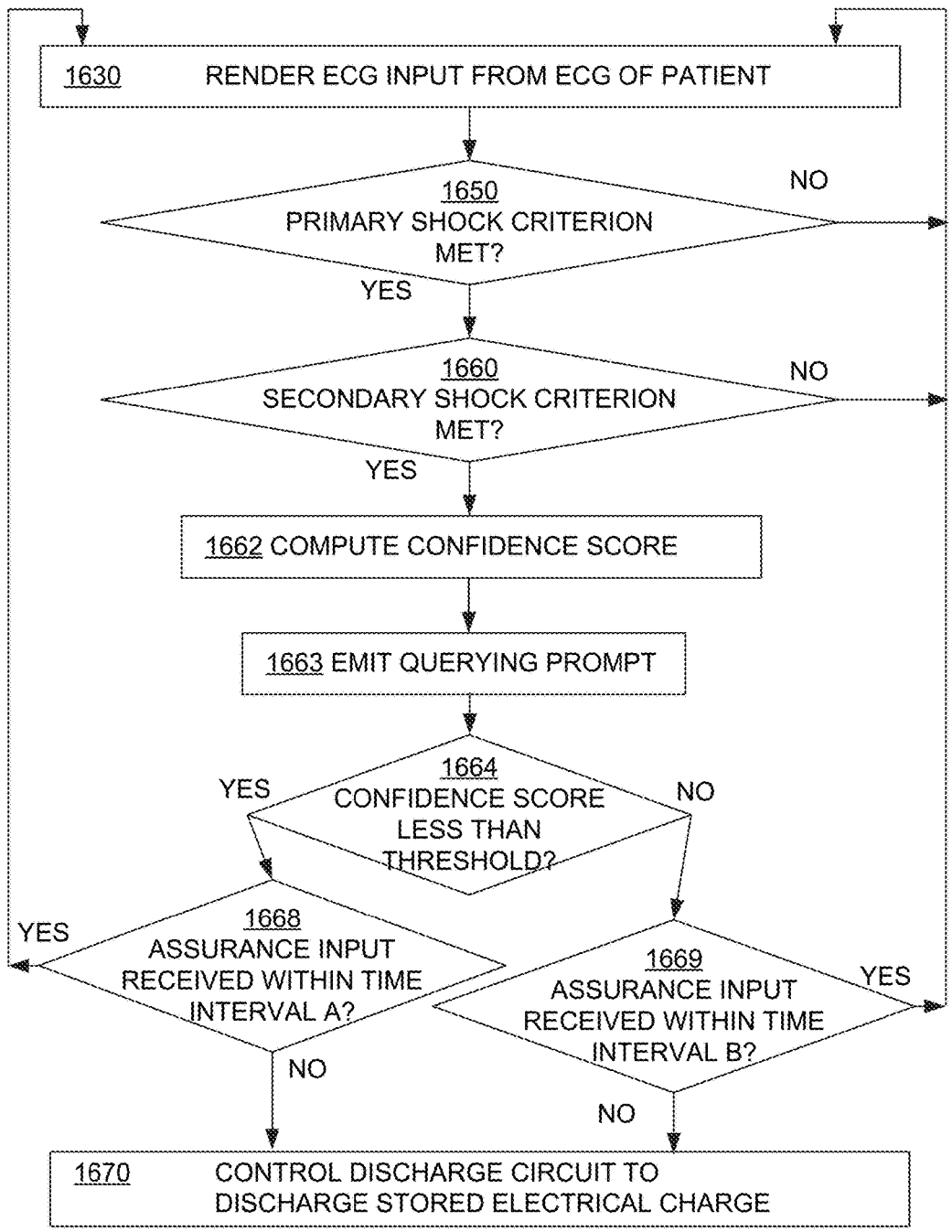
FIG. 16  *METHODS*

WEARABLE CARDIOVERTER DEFIBRILLATOR (WCD) SYSTEM USING SENSOR MODULES WITH REASSURANCE CODE FOR CONFIRMATION BEFORE SHOCK

CROSS REFERENCE TO RELATED PATENT APPLICATIONS

This patent application is a continuation of U.S. application Ser. No. 14/855,106, filed Sep. 15, 2015, which will issue as U.S. Pat. No. 9,901,741 on Feb. 27, 2018, which claims priority from US Provisional Patent Application Ser. No. 62/159,764, filed on May 11, 2015, the disclosure of which, as initially made, is hereby incorporated by reference.

BACKGROUND

When people suffer from some types of heart arrhythmias, the result may be that blood flow to various parts of the body is reduced. Some arrhythmias may even result in a Sudden Cardiac Arrest ("SCA"). SCA can lead to death very quickly, e.g. within 10 minutes, unless treated in the interim.

Some people have an increased risk of SCA. People at a higher risk include individuals who have had a heart attack, or a prior SCA episode. A frequent recommendation is for these people to receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardioverter defibrillator ("WCD") system. (Earlier versions of such systems were called wearable cardiac defibrillator ("WCD") systems) A WCD system typically includes a harness, vest, or other garment that the patient is to wear. The WCD system includes a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart.

A problem is that diagnosis for purposes of deciding whether to shock or not is not always perfectly reliable. Measures can be taken to increase the sensitivity of the detection, i.e. the ability of a test to correctly identify cardiac rhythms that require an electric shock. A challenge with increasing sensitivity, however, is that more events could be identified as shockable than actually are shockable. When this happens, the patient wearing the WCD system may be shocked needlessly, which results in discomfort and lack of desire to wear the WCD system.

A partial solution to this problem has been to enlist the patient's help in clearing events that are falsely identified as shockable. For example, some WCD systems emit an alarm warning that an event has been detected, and that an electric shock will be administered soon. Such systems also include a button that the patient may press to prevent the electric shock from being administered. This button is sometimes known as a "live man switch" or an "I am alive" switch. Even having to listen to the alarm and use this button to prevent being shocked, however, is a distraction to the patient.

BRIEF SUMMARY

The present description gives instances of wearable cardioverter defibrillator ("WCD") systems, storage media that store programs, and methods, the use of which may help overcome problems and limitations of the prior art.

In one embodiment, a wearable cardioverter defibrillator ("WCD") system includes a support structure that can be worn by a patient, and a defibrillator coupled to the support structure. An ECG input, rendered from an ECG of the patient, may meet a primary shock criterion. One or more sensor modules are further provided, which are worn by the patient at different times. The sensor modules may monitor different physiological parameters of the patient, and transmit signals about them. The WCD system further has a multi-sensor interface to receive the transmitted signals, and a processor to determine from them whether a secondary shock criterion is met. If both the primary and the secondary shock criteria are met, the decision is to shock.

An advantage over the prior art can be that the signals from the sensor modules may reveal that a shock was not merited, thus increasing the specificity of the detection. Accordingly embodiments with the higher specificity prepare to shock at fewer of the times when a shock is not truly indicated. This way, the patient will be spared the unnecessary interruption of having to hurriedly respond to the WCD system with the information that he is alive, or even being shocked unnecessarily. Another advantage may be that the patient can wear different sensor modules at different times, suitably deciding between privacy and convenience in different contexts.

These and other features and advantages of this description will become more readily apparent from the Detailed Description, which proceeds with reference to the associated drawings in which:

BRIEF DESCRIPTION OF THE DRAWINGS

FIG. 6 is a sample decision table for an operation according to embodiments.

FIG. 15 is a flowchart for illustrating methods according to embodiments where a confidence score is computed.

FIG. 16 is a flowchart for illustrating methods according to additional embodiments where a confidence score is computed.

DETAILED DESCRIPTION

As has been mentioned, the present description is about wearable cardioverter defibrillator ("WCD") systems, storage media that store programs, and methods. Embodiments are now described in more detail.

Embodiments include WCD systems, which are configured to be worn by a person. A WCD system made according to embodiments has a number of components. These components can be provided separately as modules that can be interconnected, or can be combined with other components, etc.

The person wearing the WCD system is sometimes also called a patient and/or a wearer. The person may be moving, for example during their daily activities. As they move, any garments they wear may shift with respect to their body. The wearable defibrillator systems of the embodiments are configured to defibrillate the patient by delivering an electrical charge to the patient's body.

A component of a WCD system can be a support structure, which is configured to be worn by the patient. The support structure can be any structure suitable for wearing, such as a harness, a vest, a half-vest—for example over the left side of the torso that positions electrodes on opposite sides of the heart, one or more belts that are configured to be worn horizontally or possibly vertically over a shoulder, another garment, and so on. The support structure can be implemented in a single component or multiple components. For example, a support structure may have a top component resting on the shoulders, for ensuring that the defibrillation electrodes will be in the appropriate positions for defibrillating, and a bottom component resting on the hips, for carrying the bulk of the weight of the defibrillator. A single component embodiment could be with a belt around at least the torso. Other embodiments could use an adhesive structure or another way for attaching to the patient, without encircling any part of the body. There can be other examples.

Figure 1:
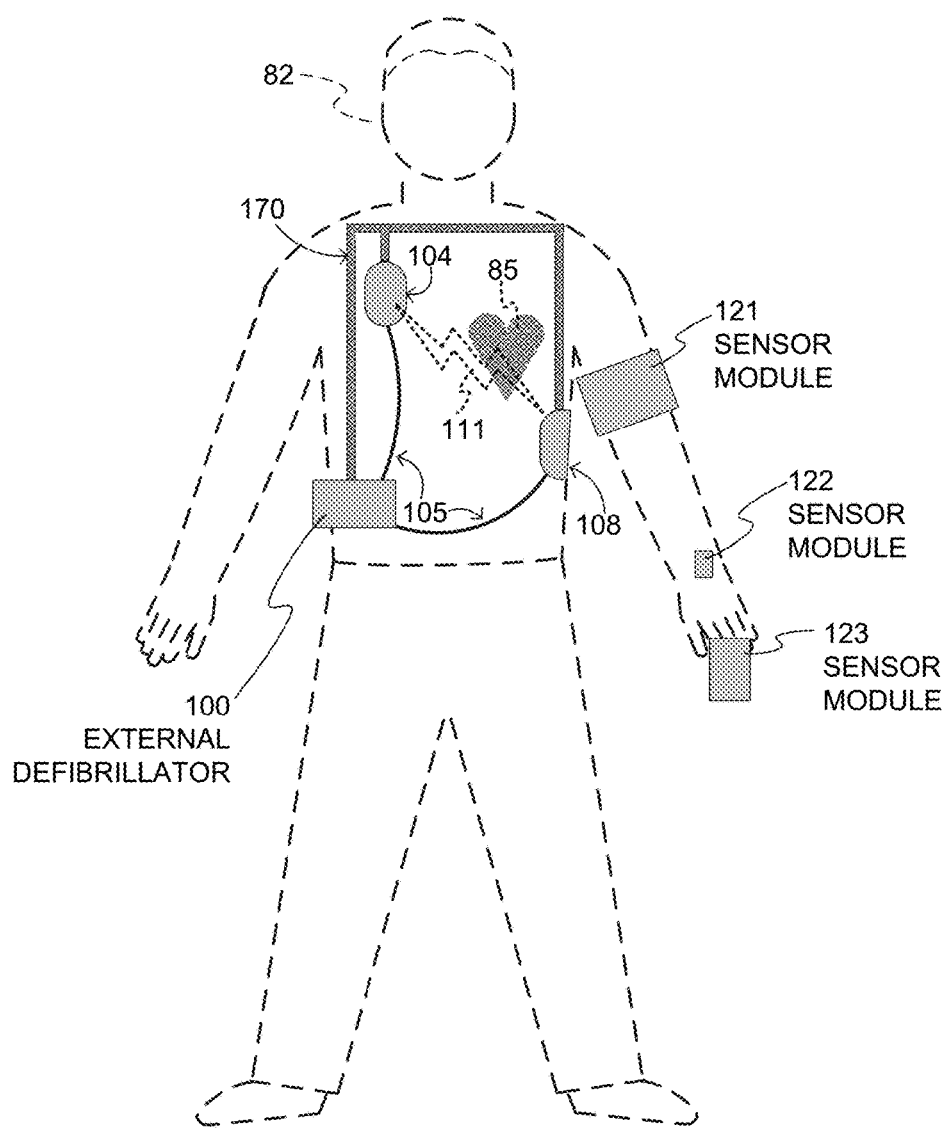
FIG. 1 is a diagram of components of a sample wearable cardioverter defibrillator ("WCD") system, made according to embodiments.

FIG. 1 depicts components of a WCD system made according to embodiments, as it might be worn by a person 82. In FIG. 1, a generic support structure 170 is shown relative to the body of patient 82, and thus also relative to his or her heart 85. Structure 170 could be a harness, a vest, a half-vest, one or more belts, or a garment, etc., as per the above. Structure 170 could be implemented in a single component, or multiple components, and so on. Structure 170 is wearable by patient 82, but the manner of wearing it is not depicted, as structure 170 is depicted only generically in FIG. 1.

A wearable cardioverter defibrillator ("WCD") system is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, many of the components of defibrillator 100 can be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as a defibrillation shock or therapy shock, is intended to go through and restart heart 85, in an effort to save the life of patient 82. Pulse 111 can further include one or more pacing pulses, and so on.

A prior art defibrillator typically decides whether to defibrillate or not based on an electrocardiogram ("ECG") signal of the patient. However, defibrillator 100 can defibrillate, or not defibrillate, also based on other inputs according to embodiments. Such inputs may increase the specificity of the WCD system, and thus treat an event as not being the type that needs to shock the patient. Examples are now described.

WCD systems according to embodiments may be further configured to be used in conjunction with one or more sensor modules. By way of an example, sensor modules 121, 122, 123 are shown in FIG. 1, and all are being used by patient 82. Additional sensor modules may be provided, such as a fourth one, etc. Such sensor modules can be motion sensors, physiological parameter sensors, etc., and be used for determining whether intervention by the WCD system is desired. In some embodiments, one or more or even all of these sensor modules are part of the WCD system.

As will be seen in more detail later in this document, these sensor modules are configured to be worn by the patient so as to monitor respective physiological parameters of the patient that can be different from each other, and other than an ECG of the patient. For example, these physiological parameters can be heart sounds of the patient, a breathing sound of the patient, a heart rate of the patient, a pulsatile blood flow of the patient, a blood oxygen level of the patient, a blood perfusion of the patient, a change in light transmission or reflection properties of perfused tissue of the patient, a color of a skin of the patient, and a motion of the patient's body. More particular sensor modules for monitoring these parameters will be described later in this document.

Such sensor modules can be worn at different times according to embodiments. An example is now described.

Figure 2:
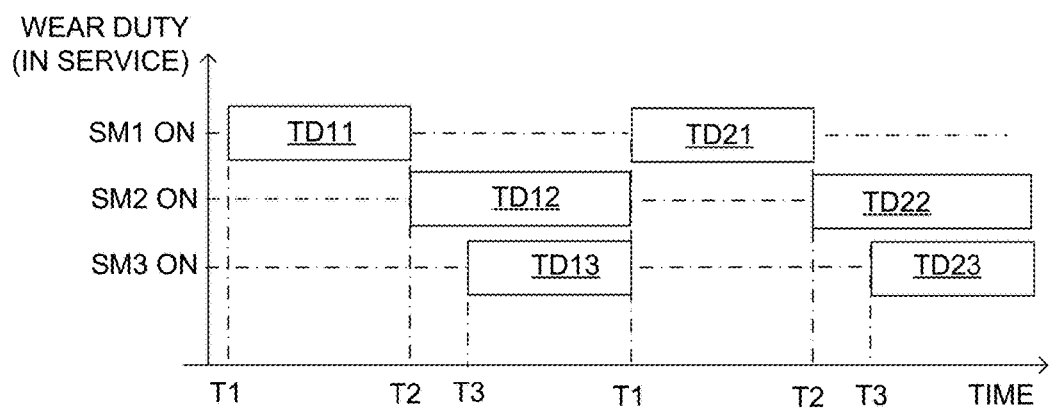
FIG. 2 is a time diagram showing a pattern of when sensor modules such as those of FIG. 1 may be worn by a patient according to embodiments.

FIG. 2 is a time diagram showing a pattern of when sensor modules such as those of FIG. 1 may be worn by a patient according to embodiments. FIG. 2 shows a time axis that spans approximately two days, and which sensor modules are used at the time. The time intercepts define time durations. These time durations are generally different from each other. Different time durations may or may not overlap. The use of three sensor modules SM1, SM2, SM3 is described in terms of their wear duty, i.e. whether they are in service for a WCD system or not. These sensor modules can be the same or different than those of FIG. 1.

Time T1 may be in the morning, when the patient gets ready for the day. He wears the first sensor module for time durations TD11 and TD21, namely from times T1 until times T2.

Time T2 may be in the evening, when the patient is back at home. He stops wearing the first sensor module, and starts wearing the second sensor module for time durations TD12 and TD22, namely from times T2 until times T1 of the next day.

Time T3 may be late in the evening, when the patient goes to sleep. He wears the third sensor module for time durations TD13 and TD23, namely from times T3 until times T1 of the next day.

Advantageously, the patient can wear different sensor modules at different times, according to their different needs. For example, while the patient is at work, a sensor module that can be worn under the garments may be preferred for increased privacy. For another example, while sleeping, a sensor module might be preferred that interferes the least with the patient's sleep.

In addition, these sensor modules can be further configured to generate respective sensing inputs from their respective monitored physiological parameters, such as voltages, currents, images, values from digital measurement systems, and so on.

Moreover, these sensor modules can be further configured to transmit respective signals that communicate their respective sensing inputs according to embodiments. These signals can be thus used by the WCD system to make a better decision. In some embodiments, these signals may encode a value of their respective physiological parameter.

In some embodiments, these signals from the sensor modules may encode an alarm generated from a value of the first sensing input. These signals may thus help with the sensitivity in detecting a cardiac arrest. It should be remembered, however, that a more definitive detection of the cardiac arrest might be from analyzing the ECG.

In some embodiments, these signals from the sensor modules may encode a reassurance code generated from a value of the first sensing input. These signals may thus help with the specificity in detecting a cardiac arrest, i.e. in preventing the false detection of cardiac arrest, such as from an ECG signal. Accordingly, signals with the reassurance code may operate as inhibit signals for shocking.

Given the high value of the ECG signal in the detection of cardiac arrest, sensor modules can be more valuable in embodiments if made so as to provide high specificity in detecting the absence of cardiac arrest. In fact, in embodiments, sensor modules that provide alarm signals are not provided. Or, where provided, it is clear in advance to the remainder of the system whether their anticipated signal is a reassurance code (inhibit) or an alarm signal.

A WCD system according to embodiments may further include a multi-sensor interface that is configured to receive the signals transmitted from the sensor modules. Embodiments of such a multi-sensor module are described in more detail later in this document. The multi-sensor interface can be configured to be worn by the patient. In FIG. 1, the multi-sensor interface receiving the signals transmitted from sensor modules 121, 122, 123 is not shown, because it is embodied within defibrillator 100.

Figure 3:
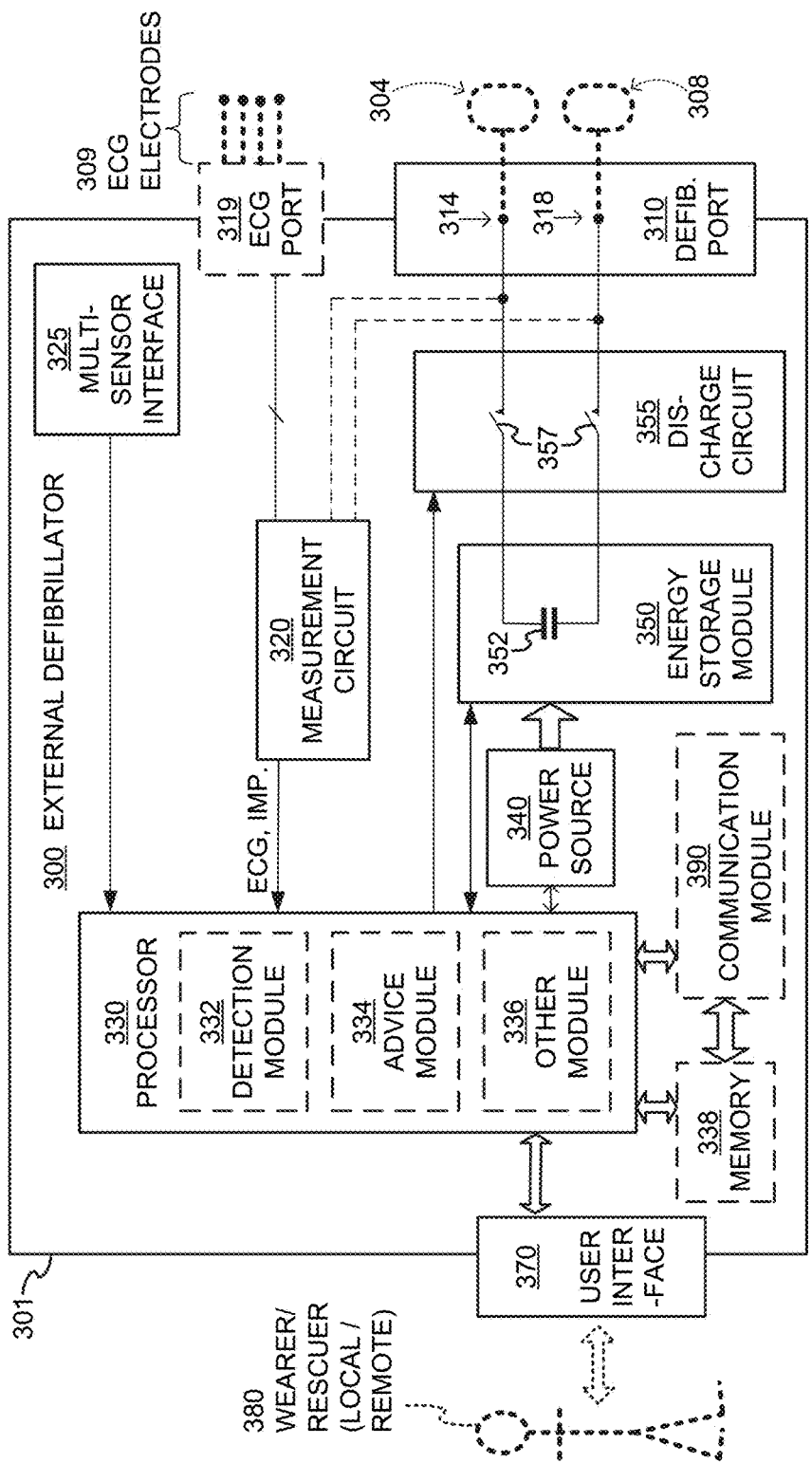
FIG. 3 is a diagram showing sample components of an external defibrillator, such as the one belonging in the system of FIG. 1, and which is made according to embodiments.

FIG. 3 is a diagram showing components of an external defibrillator 300 made according to embodiments. These components can be, for example, in external defibrillator 100 of FIG. 1. These components of FIG. 3 can be provided in a housing 301, which is also known as defibrillator housing 301 and casing 301. As seen from FIG. 1, defibrillator housing 301 can be configured to be coupled to the support structure. Moreover, the sensor modules can be configured to be worn by the patient by being outside the defibrillator housing, and sometimes not even being in physical contact with it.

External defibrillator 300 is intended for a patient who would be the wearer, such as person 82 of FIG. 1. In the shown embodiment, defibrillator 300 includes the above-mentioned multi-sensor interface 325. It will be understood that multi-sensor interface 325 need not be touching housing 301 if the signals from the sensor modules arrive wirelessly, but may protrude through housing 301 otherwise. In other embodiments, the multi-sensor interface is provided outside housing 301.

Defibrillator 300 typically includes a defibrillation port 310, such as a socket in housing 301. Defibrillation port 310 includes nodes 314, 318. Defibrillation electrodes 304, 308, which will be described later in more detail, can be plugged in defibrillation port 310, so as to make electrical contact with nodes 314, 318, respectively. It is also possible that defibrillation electrodes can be connected continuously to defibrillation port 310, instead. Either way, defibrillation port 310 can be used for guiding via electrodes to the wearer the electrical charge that has been stored in energy storage module 350.

Defibrillator 300 may optionally also have an ECG port 319 in housing 301, for plugging in ECG electrodes 309, which are also known as ECG leads. It is also possible that ECG electrodes can be connected continuously to ECG port 319, instead. ECG electrodes 309 can help sense an ECG signal, e.g. a 12-lead signal, or a signal from a different number of leads, as long as they make good electrical contact with the body of the patient.

Defibrillator 300 also includes a measurement circuit 320. Measurement circuit 320 receives physiological signals from ECG port 319, if provided. Even if defibrillator 300 lacks ECG port 319, measurement circuit 320 can obtain physiological signals through nodes 314, 318 instead, when defibrillation electrodes 304, 308 are attached to the patient. In these cases, a patient's ECG signal can be sensed as a voltage difference between electrodes 304, 308. Plus, impedance between electrodes 304, 308 can be sensed for detecting, among other things, whether these electrodes 304, 308 are not making good electrical contact with the patient's body. These physiological signals are sensed, and an ECG input can be rendered from an ECG of the patient. The ECG input can be rendered by measurement circuit 320 as data, or other signals, etc.

Defibrillator 300 also includes a processor 330. Processor 330 may be implemented in any number of ways. Such ways include, by way of example and not of limitation, digital and/or analog processors such as microprocessors and digital-signal processors ("DSP"s); controllers such as microcontrollers; software running in a machine; programmable circuits such as Field Programmable Gate Arrays ("FPGA"s), Field-Programmable Analog Arrays ("FPAA"s), Programmable Logic Devices ("PLD"s), Application Specific Integrated Circuits ("ASIC"s), any combination of one or more of these, and so on.

Processor 330 can be considered to have a number of modules. One such module can be a detection module 332. Processor 330, running detection module 332, is a sample embodiment of a logic device configured to determine whether the above-described monitored parameter has reached a specific threshold. For example, the monitored parameter can be input from sensor modules 121, 122, or others if provided. For another example, detection module 332 can include a Ventricular Fibrillation ("VF") detector and the patient's sensed ECG from measurement circuit 320 can be used to determine whether the patient is experiencing VF. Detecting VF is useful, because VF is a precursor to SCA.

Another such module in processor 330 can be an advice module 334, which arrives at advice, for example based on outputs of detection module 332, and/or implements decisions. There can be many types of advice according to embodiments. As one example, a Shock Advisory Algorithm can render the advice to shock, as opposed to not shock the patient. Shocking can be for defibrillation, pacing, and so on. If the advice is to shock, some external defibrillator embodiments proceed with shocking, or may advise a remote attendant to do it, and so on. As another example, the advice can be to administer CPR, and defibrillator 300 may further issue prompts for it, and so on.

Processor 330 can include additional modules, such as module 336, for other functions. In addition, processor 330 may perform the functions of interpreting the signals received from the sensor modules.

Defibrillator 300 optionally further includes a memory 338, which can work together with processor 330. Memory 338 may be implemented in any number of ways. Such ways include, by way of example and not of limitation, nonvolatile memories ("NVM"), read-only memories ("ROM"), random access memories ("RAM"), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for person 380, if they are a local rescuer. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include an AC power override, for where AC power will be available, and so on. In some embodiments, power source 340 is controlled by processor 330.

Defibrillator 300 additionally includes an energy storage module 350 within defibrillator housing 301. Module 350 is where some electrical energy can be stored, when preparing it for sudden discharge to administer a shock. Module 350 can be charged from power source 340 to the right amount of energy, as controlled by processor 330. In typical implementations, module 350 includes a capacitor 352, which can be a single capacitor or a system of capacitors, and so on.

Defibrillator 300 moreover includes a discharge circuit 355. Discharge circuit 355 can be configured to discharge the electrical charge stored in energy storage module 350 through the patient's body. More particularly, circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for a user 380. User 380 can be the wearer, if conscious, or a rescuer. The rescuer can be local, such as a bystander who might offer assistance, or a trained person who might arrive after the fact. Alternately the rescuer could be remote, such as a trained person in remote communication with a system according to embodiments, and/or with the wearer. User interface 370 can thus instruct or remind patient 82 about properly wearing sensor modules 121, 122, 123.

User interface 370 can be configured to emit prompts towards the patient, and receive input from the patient. For example, user interface 370 can be configured to emit a querying prompt, such as ask a question ("Are you alive?"). Moreover, user interface 370 can be configured to receive an assurance input, equivalent to saying: "I am alive", for example by including the previously mentioned "live man switch" or "I am alive" switch.

User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, touchscreens, a microphone, and so on to receive the patient inputs. In addition, discharge circuit 355 can be controlled by processor 330, or directly by user 380 via user interface 370, and so on.

Defibrillator 300 can optionally include other components. For example, a communication module 390 may be provided for communicating with other machines or a remote rescuer 380. Such communication can be performed wirelessly, or via wire, or by infrared communication, and so on. This way, data can be communicated, such as patient data, episode information, therapy attempted, CPR performance, and so on. In some embodiments, communication module 390 performs one or more of the functions of the multi-sensor interface, and then multi-sensor interface 325 is not provided separately as shown.

A WCD system according to embodiments may additionally include defibrillation electrodes. It will be appreciated that the defibrillation electrodes of embodiments could both deliver a charge, and also serve for sensing the patient's ECG. The defibrillation electrodes can deliver to the patient an electrical charge stored in the capacitor, for restoring their heart rhythm, when the defibrillation electrodes make good electrical contact with the body of the patient.

In the example of FIG. 3, defibrillation electrodes 304, 308 may plug into defibrillation port 310, so as to make electrical contact with nodes 314, 318, respectively. Defibrillation electrodes 304, 308 could be similar to defibrillation electrodes 104, 108 of FIG. 1.

A WCD system according to embodiments may additionally include ECG electrodes. If provided, ECG electrodes could be electrically connected for example as seen in FIG. 3 for ECG electrodes 309.

As such, in many embodiments, either defibrillation electrodes are provided by themselves, or ECG electrodes are provided in addition to defibrillation electrodes. An ECG reading can be provided by either type of electrodes, preferably while they are making good electrical contact with the body of the patient, and more particularly the skin.

In embodiments, the processor is configured to determine from the ECG input whether or not a primary shock criterion is met, as is explained in more detail later in this document. If it is so determined, then the processor is further configured to determine whether or not a secondary shock criterion is met, as is explained in more detail later in this document. This latter determination may be made from one or more signals transmitted by the sensor modules and received by the multi-sensor interface. Moreover, the processor can be configured to control the discharge circuit to discharge the stored electrical charge through the patient's body, if both the primary and the secondary shock criteria are met. In some embodiments, when the decision is to shock, an electrical charge is delivered to the patient. Delivering the electrical charge is also known as discharging. Shocking can be for defibrillation, pacing, and so on.

In embodiments, one or more of the components of the shown WCD system have been customized for the patient. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make any interim diagnoses more accurate, since bodies behave differently. For example, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Figure 4:
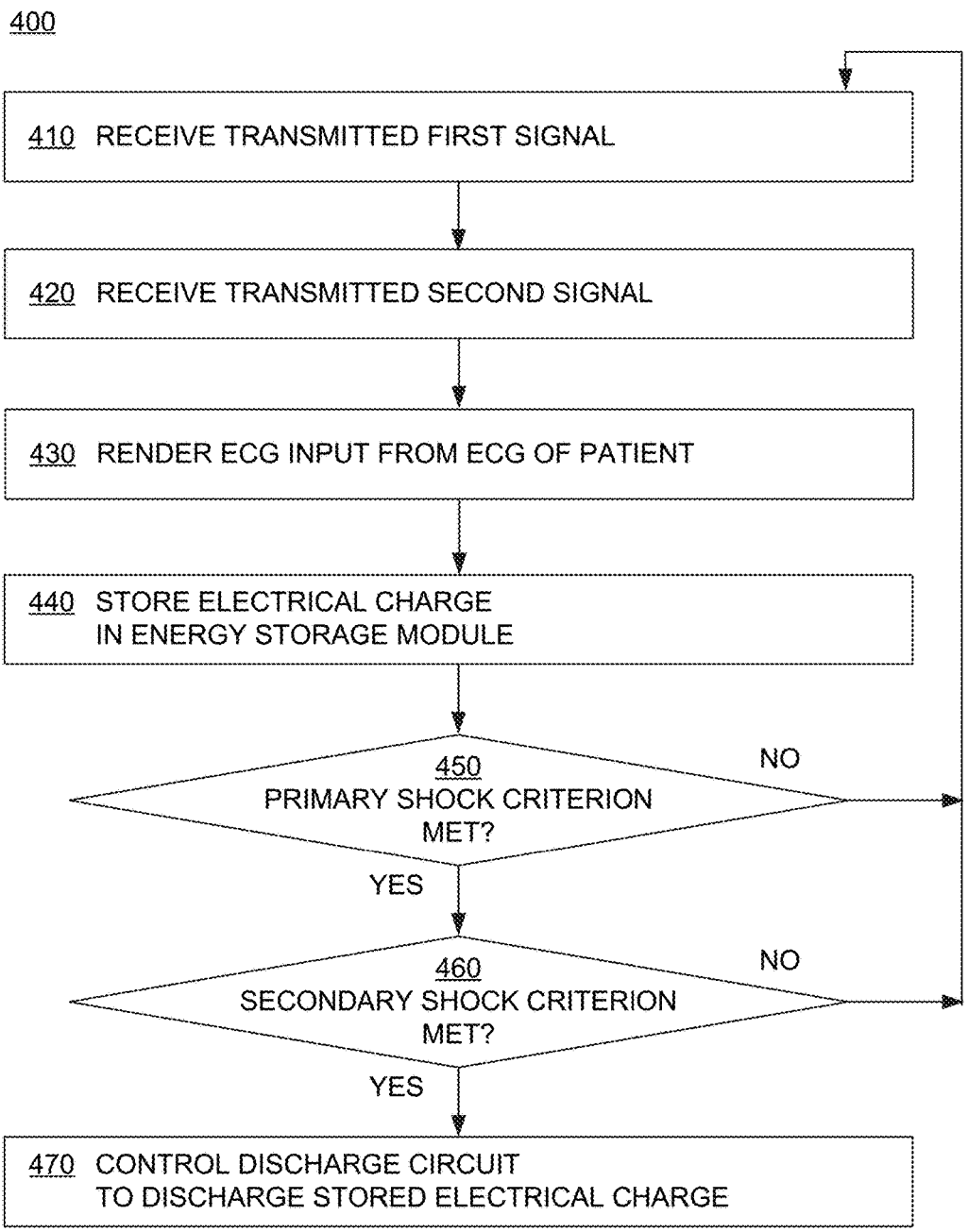
FIG. 4 is a flowchart for illustrating methods according to embodiments.

Methods are now described. FIG. 4 shows a flowchart 400 for describing methods according to embodiments. According to an operation 410, a first signal can be received by a multi-sensor interface, which is transmitted from a first sensor module. According to another operation 420, a second signal can be received by the multi-sensor interface, which is transmitted from a second sensor module.

It is understood that operations 410, 420 may take place at different times. For example, referring briefly to FIG. 2, during time duration TD11, operation 410 may be performed several times by itself. Between times T2 and T3, operation 420 may be performed several times by itself, and so on. For another example, during time duration TD13, service modules SM2 and SM3 may be considered the first and the second module, and thus operations 410 and 420 may be performed multiple times.

Returning to FIG. 4, according to another operation 430, an ECG input may be rendered from an ECG of the patient by a measurement circuit. According to another operation 440, an electrical charge may become stored in an energy storage module.

According to another operation 450, it can be determined from the ECG input whether or not a primary shock criterion is met. Typically, the primary shock criterion is a shockable ECG rhythm. If not, execution may return to a previous operation, such as operation 410.

If yes then, according to another operation 460, it can be further determined whether or not a secondary shock criterion is met. The determination of operation 460 may be made from at least one of the received first signal and the received second signal of operations 410 and 420. Given that, as per the above, such signals may be received concurrently or not, preference may be given to those of the signals received more recently. In addition, there can be rules as to what to do if the signals conflict, and so on, as will be seen later in this document.

Typically the secondary shock criterion of operation 460 either corroborates that the patient needs to be shocked, or establishes that the first shock criterion being met at operation 450 was a false alarm. For example, this secondary shock criterion can be that inhibit signals have not been received from any of the sensor modules. So, if the secondary shock criterion is not met, execution may return to a previous operation, such as operation 410.

If the secondary shock criterion is indeed met then, according to another operation 470, the discharge circuit can be controlled to discharge the stored electrical charge through the patient's body. Accordingly, operation 470 can take place if both the primary and the secondary shock criteria are met. Of course, before shocking, the patient may be additionally queried first, and so on, as will be further described with reference to FIGS. 15 and 16.

The operations of flowchart 400 may be performed in a number of ways. Examples are now described.

Figure 5:
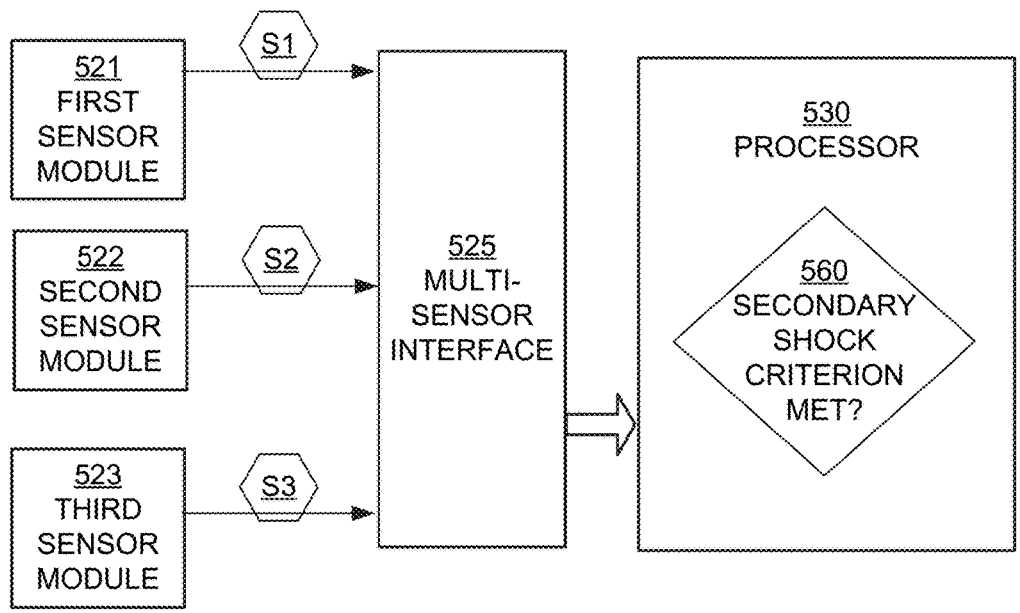
FIG. 5 is a diagram showing an example of how multiple different signals may be used to make a determination according to embodiments.

FIG. 5 shows three sample sensor modules 521, 522, 523 according to embodiments. These have respective names like "first", "second", etc. Of course, they can be characterized as first, second, etc. in any order. They can monitor patient parameters as per the above. Accordingly, sensor modules 521, 522, 523 may be further configured to transmit respective signals S1, S2, S3 that are generated from the respective parameters they monitor. So, first sensor module 521 may make available a first signal S1 generated from the first parameter, second sensor 522 module may make available a second signal S2 generated from the second parameter, and so on.

It will be understood that, while one of the sensor modules is worn, it may transmit its signal more than once. In fact, it can transmit updated signals, which can update with later values of the monitored patient parameter, during extended times, for example during at least one hour. The updated signals can be transmitted occasionally, for example only when the value changes. Or substantially periodically, and the period can be, for example, every 10-60 sec.

Transmitting can be autonomously initiated by the sensor module. Or, it can be in response to a polling signal. For example, a processor of a WCD system can be configured to cause a polling signal to be transmitted, for example via the multi-sensor interface. The signals from the sensor module can be initiated, and therefore received by the multi-sensor interface, responsive to the sensor module receiving the polling signal. In some embodiments, the polling signal is transmitted substantially periodically during at least one hour. In some embodiments, the polling signal is transmitted if the ECG input meets an alert condition, and checking is desired.

A WCD system according to embodiments may also include a multi-sensor interface 525. A sample such multi-sensor interface 325 was shown in FIG. 3. Multi-sensor interface 525 can be configured to receive one or more of the signals that are transmitted by sensor modules 521, 522, 523.

A WCD system according to embodiments may further include a processor 530. A sample such processor 330 was shown in FIG. 3. Multi-sensor interface 525 may receive signals S1, S2, S3 transmitted by sensor modules 521, 522, 523, and pass them on to processor 530. Processor 530 can be configured to make a determination 560 from the content of signals S1, S2, S3. Determination 560 can be similar to the determination of operation 460.

Operation 460 may be performed in a number of ways. Examples are now described.

In some embodiments, only one signal is used to determine whether the secondary shock criterion is met. For example, during time duration TD21 of FIG. 2, one signal is available only. Earlier, other signals may have been received, and their values can be recorded and consulted. Their recorded values can be discounted or ignored, however, given that they were received longer than a recent time interval prior. Accordingly, the only signal that remains will be used.

In some embodiments, it is determined whether the secondary shock criterion is met from at least two of the received signals. These can be the first and the second signals. Or, it can be the third plus the first or the second, and so on. The determination may be made according to a decision table, a voting scheme such as a weighted voting scheme, and so on. Examples are now described.

FIG. 6 is a sample decision table 660 for performing operation 460 according to an embodiment. In FIG. 6, all three signals S1, S2, S3 are received from three sensor modules, for four different scenarios. Table 660 can be adjusted to fewer or more signals, by removing or adding columns according to the same pattern.

Table 660 can be used with the notion that signals S1, S2, S3 affirmatively convey assurance or not. Of course, in equivalent implementations, the notion could be used as to whether signals S1, S2, S3 convey alarm instead of assurance, and so on.

Assurance can be conveyed by each of signals S1, S2, S3 themselves carrying a reassurance code. Or, signals S1, S2, S3 may convey values for their physiological parameters that correspond to assurance, for example if they meet thresholds, in which case the processor will determine that reassurance is merited.

In the example of FIG. 6, it is required that all available signals convey assurance for the secondary shock criterion to not be met. If any one of them does not provide assurance, the secondary shock criterion is met and the shock is delivered to the patient, perhaps after warning, etc.

In other embodiments where multiple signals are present, a voting scheme may be used. For example, each signal may be given a vote, as to whether it conveys assurance, and the total votes are counted to see if they exceed a threshold. Each vote could count the same regardless of which signal it came from. Or, the votes could be weighed so that they are unequal to each other, according to the relative reliability of the monitored parameter of the signal they came from.

In embodiments, multi-sensor interface 525 is versatile, in that it can receive the transmitted signals. And, as was seen in FIG. 2, which signal is transmitted and received can change during a single day, while the patient could be wearing the WCD system continuously. Accordingly, it can be determined whether the secondary criterion is met from the available signals at the time, as mentioned above.

Sometimes, it is possible that the patient will have stopped wearing any of the sensor modules, while continuing to wear the remainder of the WCD system. In such cases, after some time, a WCD system according to embodiments may fairly consider such signals to be stale and thus unreliable for use determining whether or not the secondary shock criterion is met. This might not be a problem as long as the primary shock criterion of operation 450 is not met.

If, however, the primary shock criterion is met, and if none of the signals have been received for a first time interval then, in some embodiments, the discharge circuit can be controlled to discharge the stored electrical charge through the patient, regardless of whether or not the secondary shock criterion is met. The first time interval can be set to a suitable duration, for example corresponding to how frequently the signals are expected.

In some embodiments, the WCD system can request a signal from the sensor modules by transmitting a polling signal and then waiting for an appropriate amount of time. This can take place routinely, periodically, or only if the primary shock criterion is met. In such embodiments, if none of the signals have been received for a second time interval, a polling signal can be caused to be transmitted. Then, if no signal has been received for a third time interval after the polling signal has been transmitted, the discharge circuit can be controlled to discharge the stored electrical charge through the patient if the primary shock criterion is met, regardless of whether or not the secondary shock criterion is met.

In some embodiments, the WCD system might not be able to have adequate confidence in the signals it receives from the sensor modules. And it might need such confidence, especially in the context where these signals encode reassurance codes. In such embodiments, the processor might compute a confidence score from the signal it receives. For example, the computed confidence score can be higher if it is computed from both a received first signal and a received second signal, than if it were computed from either one of them, especially if both these signals indicate the same way. Or, the computed confidence score can be higher if it is computed from a signal that has been received more recently, than less recently.

The different confidence scores maybe used in different ways, for example in querying the patient in different ways, if the secondary shock criterion is met. Querying may be by emitting querying prompts, and may invite the patient to use the "I am alive" switch as a way of providing an assurance input. Querying, however, may have a different urgency or expectation of a response depending on whether the confidence score is above or below a threshold, etc. Examples are now described.

In some embodiments, the user interface can be caused to emit a first querying prompt if the confidence criterion is below a first threshold, and a second querying prompt different from the first querying prompt if the confidence criterion is above the first threshold. The discharge circuit can be controlled to discharge the stored electrical charge if an assurance input is not received responsive to the emitted one of the first querying prompt and the second querying prompt. An example is now described.

Referring to FIG. 15, a flowchart 1500 is shown. Some of the operations of flowchart 1500 can be performed in conjunction with other operations, for example the operations of FIG. 4. In addition, operations 1530, 1550, 1560 and 1570 may be performed as described for operations 430, 450, 460 and 470 respectively.

At operation 1562, a confidence score may be computed. At operation 1564, it is determined whether the computed confidence score is less than a threshold. If so then, at operation 1566, a first querying prompt A is emitted. If not then, at operation 1567, a second, different querying prompt B is emitted. Then, at operation 1568 it is determined whether an assurance input is received, for example by the patient actuating the "I am alive" switch of the user interface. If not, then execution may revert to operation 1530; else it may proceed to operation 1570.

In some embodiments, the user interface can be caused to emit a querying prompt. The discharge circuit can be controlled to discharge the stored electrical charge at different times, depending on the confidence score. For example, if the confidence criterion is below a certain threshold, the discharge circuit can be controlled to discharge the stored electrical charge if an assurance input is not received after a first time interval, responsive to the emitted querying prompt. Else, if the confidence criterion is above the certain threshold, the discharge circuit can be controlled to discharge the stored electrical charge if an assurance input is not received after a second time interval different from the first time interval, responsive to the emitted querying prompt. An example is now described.

Referring to FIG. 16, a flowchart 1600 is shown. Some of the operations of flowchart 1600 can be performed in conjunction with other operations, for example the operations of FIG. 4. In addition, operations 1630, 1650, 1660, 1662 and 1670 may be performed as described for operations 430, 450, 460, 1562 and 470 respectively.

At operation 1663, a querying prompt is emitted. If, at operation 1664, the confidence score is less than a certain threshold then, according to operation 1668, it is inquired whether an assurance input has been received within a first time interval A. Else if, at operation 1664, the confidence score is larger than the certain threshold then, according to operation 1669, it is inquired whether an assurance input has been received within a second, different time interval B. If the assurance input is received within its waited-for time interval, then execution may revert to operation 1630; else it may proceed to operation 1670.

Accordingly, if the WCD has received a very recent inhibit signal from one of the sensor modules, it could be more persistent and patient in requesting and waiting for the wearer to respond. Or it could issue a less harshly worded prompt to check the contact of the garment with their skin, or to pause the activity they are doing for a good ECG reading. The prompt could be, for example, "I'm confused by the signals I am receiving, could you stop what you are doing for a minute while I re-evaluate your heart rhythm?" Perhaps this is how it would handle a situation where it has only one sensor module giving an inhibit signal. A different device reaction could be given if there are more than one inhibit signals coming from sensor modules (perhaps only prompting for adjusting or replacing the garment).

Embodiments of the multi-sensor interface are now described in more detail. In general, a multi-sensor interface according to embodiments can be configured to be worn by the patient by being configured to be coupled to the support structure, for example by being implemented as a standalone device.

In some embodiments, the multi-sensor interface can be located entirely within the defibrillator housing, such as was shown in FIG. 3. This can operate well where the transmitted signals are configured to be received wirelessly, for example using Bluetooth, Radio Frequency Identification ("RFID"), etc., each time with appropriate pairing to ensure the integrity of the communication of the signal. The RFID implementation may be with the sensor module writing to its own RFID tag the value of the time, and permitting the sensor interface to use an RFID reader to query the RFID tag.

In some embodiments, the multi-sensor interface can be located partially within the defibrillator housing, and partially protrude from it. This can operate well where the transmitted signals are configured to be received via one or more wires. Examples are now described.

Figure 7:
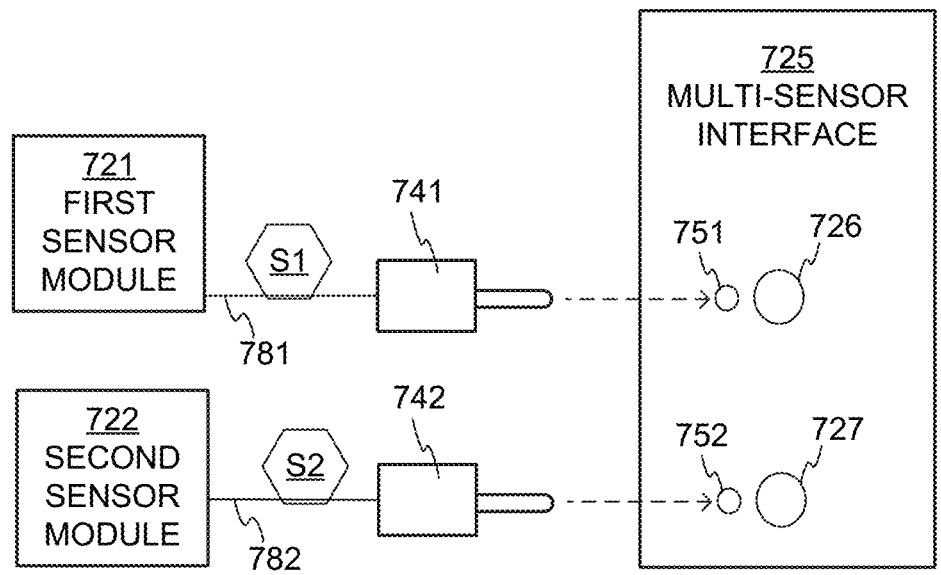
FIG. 7 is a diagram of a sample multi-sensor interface configured to receive signals from two sensor modules concurrently according to embodiments.

FIG. 7 is a diagram of a sample multi-sensor interface 725. Multi-sensor interface 725 can be configured to receive signals S1, S2 from a first sensor module 721 and a second sensor module 722. It will be understood that signals S1, S2, etc., may be the same or different across various ones of the drawings of this description.

In FIG. 7, signals S1, S2 are received concurrently. In particular, sensor modules 721, 722 have respective plugs 741, 742 carried by wires 781, 782. Multi-sensor interface 725 has two sockets 751, 752, that can receive plugs 741, 742 as shown.

Multi-sensor interface 725 also has a first visual indicator 726 near socket 751, which can be an LED or equivalent. Visual indicator 726 can be configured to become activated by being lit, and so on. Visual indicator 726 can be configured to become activated responsive to signal S1 being received, so as to indicate that signal S1 is being received via socket 751. In methods, visual indicator 726 can be caused to become activated responsive to the signal S1 being received. Multi-sensor interface 725 further has a second visual indicator 727 near socket 752. Visual indicator 727 is similarly configured to become activated responsive to signal S2 being received, so as to indicate that signal S2 is being received via socket 752.

In the example of FIG. 7, sockets 751, 752 are not shown as dedicated to sensor modules 721, 722. Plugs 741, 742 could have alternately been plugged in sockets 752, 751, respectively. A socket can be made dedicated to a plug, preferably by giving both of them custom complementary shapes, different for the other pairs of plugs/sockets. The patient would then find them easy to match. Making them not dedicated may impose more requirements, for example either each signal would have to identify what parameter it is monitoring for further processing, or have the signal encode an alarm only, and the alarms could be uniform.

Sensor modules 721, 722 can monitor the same or a different parameter. For example they could both monitor motion, perhaps at different places of the patient's body. Identical motion patterns could then be attributed to environment, such as a mode of transportation, etc. Or one sensor modules could monitor motion, and another blood flow, etc. In addition, embodiments could also be using a third sensor module, a fourth sensor module, and so on, in addition to the first two sensor modules.

Figure 8:
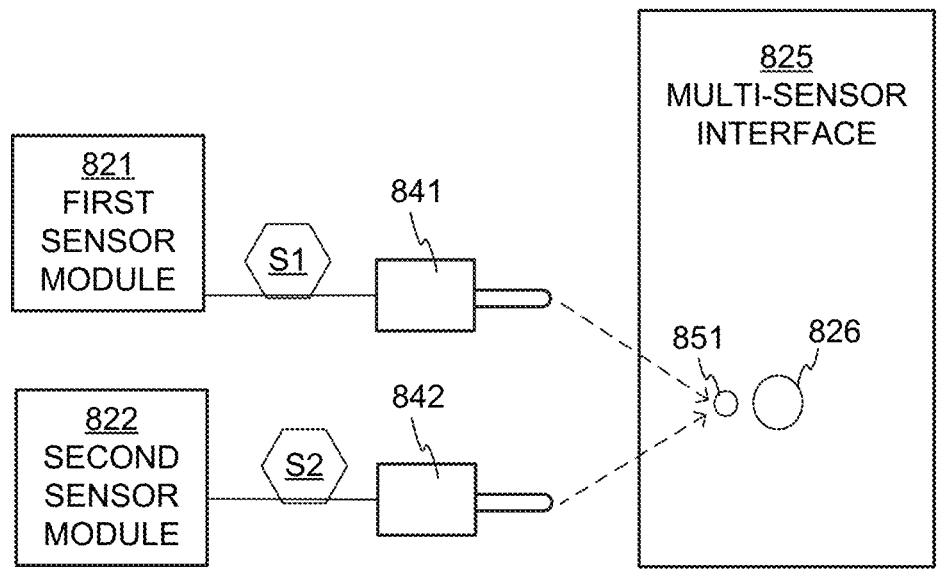
FIG. 8 is a diagram of a sample multi-sensor interface configured to receive a signal from one of two sensor modules according to embodiments.

FIG. 8 is a diagram of a sample multi-sensor interface 825. Multi-sensor interface 825 has a socket 851, and visual indicator 826 configured to become activated responsive to a signal being received, so as to indicate that a signal is being received via socket 851. Socket 851 is not dedicated; it can receive either signal S1 from first sensor module 821 via plug 841, or signal S2 from second sensor module 822 via plug 842, depending on which sensor module the patient uses at the time.

The wired implementations of FIGS. 7 and 8 may have certain advantages and disadvantages compared to wireless implementations. A wired implementation provides wires with which the patient must deal with while wearing, such as wires 781, 782. In addition, a wired system may present the risk that the patient may forget about plugging the plugs into the sockets of the multi-sensor interface. Of course, the latter risk can be addressed by a user interface of the WCD system, implemented either in the worn components or in a stationary base, issuing prompts and reminders to the patient. An advantage of a wired system is that the WCD system can provide power to the sensor module. Another advantage of a wired system is that there is clarity in defining which sensor modules are being used at any one time, both in the mind of the patient who can confirm which wires are plugged in, and also for the WCD system in discerning which sensor modules are in service, from their received signals. Indeed, when a patient stops wearing a wireless sensor module, a challenge is that the WCD system somehow has to know to stop considering its input. This challenge can be addressed as described later in the document.

Sensor modules according to embodiments are now described in more detail. These can be stand-alone devices that are part of, or separate from, the WCD system. In particular, a sensor module according to embodiments may be implemented by commercially available devices that are portable, such as smartphones, and even wearable, such as watches, wristbands, anklets, bracelets, etc. Such devices may be general-purpose, and be made usable by the WCD system by having a custom software application loaded thereon. In view of this description, it will be recognized that a software application ("app") can be written that can convert a general-purpose commercially available electronic device into a sensor module usable by a WCD system according to embodiments. In addition, such devices can be disguised to appear like bracelets, wristbands, necklaces, or concealed, by being wrapped around an ankle.

Figure 9:
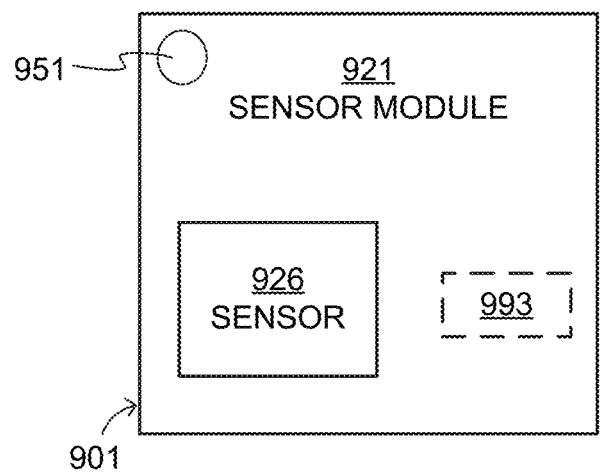
FIG. 9 is a diagram of components of a sample sensor module made according to embodiments.

FIG. 9 is a diagram of components of a sample sensor module 921 made according to embodiments. Sensor module 921 includes a sensor housing 901 that is configured to be worn by the patient. In most of these embodiments, the sensor housing is distinct from the defibrillator housing. The shape of sensor housing 901 may be dictated by the part of the patient's body that sensor module 921 will be worn at. In addition, sensor housing 901 may include a strap, a clip, a belt, Velcro, and other components and materials for configuring it to be worn by the patient, for example as mentioned above.

Sensor module 921 also includes a sensor 926. Sensor 926 can be coupled to sensor housing 901, for example by being attached to it or being completely inside it, etc. Sensor 926 can be configured to monitor the physiological parameter of sensor module 921 while sensor housing 901 is worn by the patient.

Moreover, sensor module 921 may include components for generating sensing inputs from the physiological parameter monitored by sensor 926, and for creating a signal for sensor module 921 that encodes a value for the physiological parameter, or an alarm or a reassurance code, etc. Such components may include an on-board processor, a battery, and so on. In other embodiments, sensor module 921 has fewer active components, and is queried by the WCD system.

Sensor module 921 may further include a communication device 993 that is configured to transmit the signal of sensor module 921. This can be implemented in a number of ways. For one example, communication device 993 can be configured to transmit the signal wirelessly; it may include an antenna, components to drive the antenna with a driver signal, and so on. For another example, communication device 993 can be configured to transmit the signal by wires. Transmission can be by affirmatively driving a signal, or by passively presenting some value of resistance, capacitance or charge, which the WCD system can query, whether in analog or in digital domain, etc.

Communication device 993 can be configured to transmit the signal substantially periodically, for example during at least one hour. In methods, communication device 993 can be caused to transmit signal S1. Signal S1 may be transmitted autonomously. Or, sensor module 921 can be configured to receive a polling signal, for example via communication device 993. In such embodiments, communication device 993 can be configured to transmit the signal responsive to sensor module 921 receiving the polling signal.

Sensor module 921 may additionally include an active visual indicator 951. Active visual indicator 951 can be configured to indicate that the signal of sensor module 921 is transmitted, in connection with that signal being transmitted. In methods, active visual indicator 951 can be caused to become activated in connection with signal S1 being transmitted.

In some embodiments, the monitored patient physiological parameter is a motion of the patient's body. In such embodiments, the sensor module includes a motion detector.

In some embodiments, the monitored patient physiological parameter is heart sounds, a heart rate, a breathing sound or a pulsatile blood flow of the patient. In such embodiments, the sensor module includes a microphone. For heart sounds, a library of heart sounds may also be provided, etc.

In some embodiments, the monitored patient physiological parameter is a heart wall motion consistent with reasonable cardiac coordination and function. In such embodiments, the sensor module includes an ultrasound detector, for example in a module worn on the chest.

In some embodiments, the monitored patient physiological parameter is a pulsatile blood flow of the patient. In such embodiments, the sensor module includes a Doppler device.

In some embodiments, the monitored patient physiological parameter is a heart rate, a pulsatile blood flow, or a blood pressure of the patient. In such embodiments, the sensor module includes a cuff.

In some embodiments, the monitored patient physiological parameter is a heart rate, a pulsatile blood flow, a blood pressure, a blood oxygen level, a blood perfusion or a change in light transmission or reflection properties of perfused tissue of the patient. In such embodiments, the sensor module includes a light source that is configured to illuminate tissue of the patient, for example configured as a pulse oximeter, etc. Pulsatile blood flow can be detected by an optical detector worn on a finger, wrist, ankle, headband, or in ear (embedded in a hearing aid, or in an expanding ear-plug sort of thing).

In addition, pulse detection is taught at least in Physio-Control's U.S. Pat. No. 8,135,462, which is hereby incorporated by reference in its entirety. Moreover, a person skilled in the art may implement other ways of performing pulse detection.

In some embodiments, the monitored patient physiological parameter is a color of a skin of the patient. This is useful because a white person's skin color turns ashen when they suffer from an SCA. In such embodiments, the sensor module includes a light source and a detector that is configured to detect the skin color of the patient. An example is now described.

Figure 10:
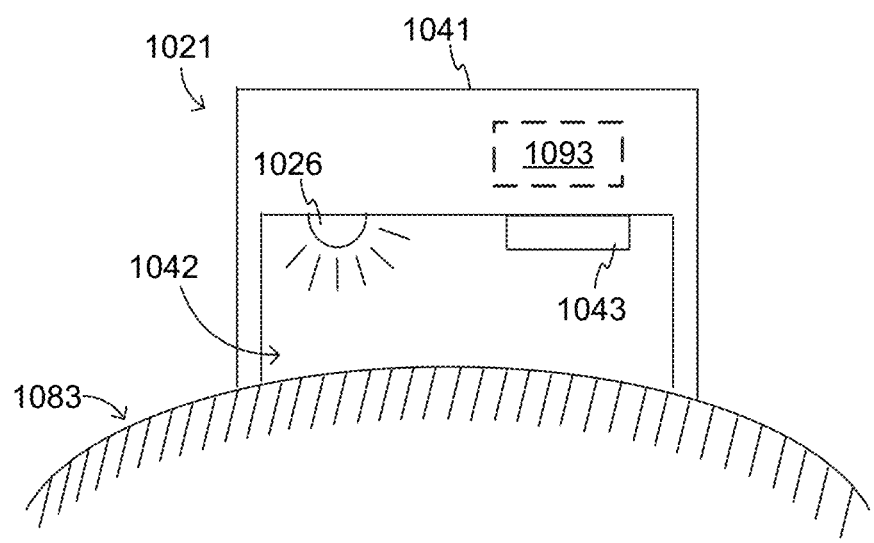
FIG. 10 is a diagram of a sample sensor module made according to embodiments.

FIG. 10 is a diagram of a sensor module 1021 made according to embodiments, which has been placed on skin 1083 of a patient. Sensor module 1021 has a sensor housing 1041 that is held against skin 1083, such as by being attached thereon by tape or an elastic band, neither of which is shown. In this embodiment, sensor module 1021 may define a cavity 1042, and only the rim of cavity 1042 contacts skin 1083. Sensor module 1021 may also have a light source 1026 that illuminates cavity 1042, and thus also illuminates the portion of skin 1083 surrounded by the rim of cavity 1042. Sensor module 1021 may further have a small imager 1043 for imaging the illuminated skin portion, for purposes of detecting its color. Imager 1043 can be made by a few pixels or one or more photodetectors. If or when the skin of a white patient turns ashen color, it is bound to reflect less white light than previously. Sensor module 1021 may also include a communication device 1093 and other components.

In some embodiments, the monitored patient physiological parameter is a respiration of the patient. In such embodiments, the sensor module includes an elastic band that is configured to be placed so as to be part of a loop around a chest of the patient. An example is now described.

Figure 11A:
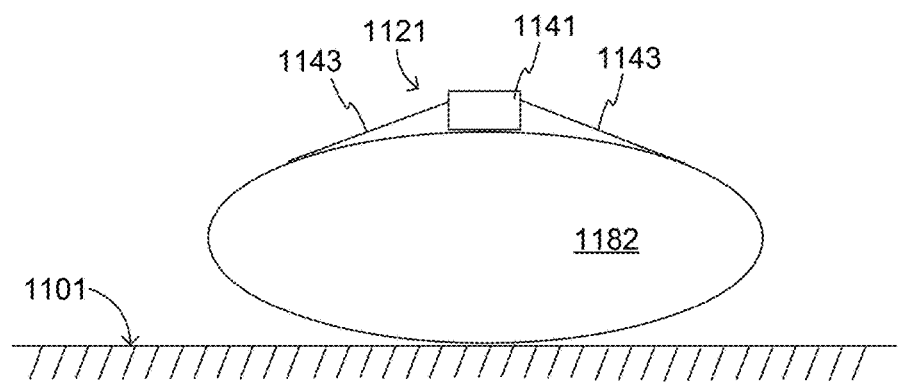
FIG. 11A is a diagram of a sample sensor module made according to embodiments, being used by a patient who is sleeping.

FIG. 11A is a diagram of a sensor module 1121 made according to embodiments, which is being used by a patient 1182 who is sleeping on a surface 1101. A section view of the torso of patient 1182 is shown. Sensor module 1121 has a sensor housing 1141 that is held against the torso by an elastic band 1143. Elastic band 1143 may be long enough to form an entire loop be around the chest of patient 1182. Alternately, a remainder of the loop may be formed by one or more other members, which may be elastic or not. The patient's breathing thus may stretch and release the band. This stretching and releasing may be detected in a number of ways, and an example is now described.

Figure 11B:
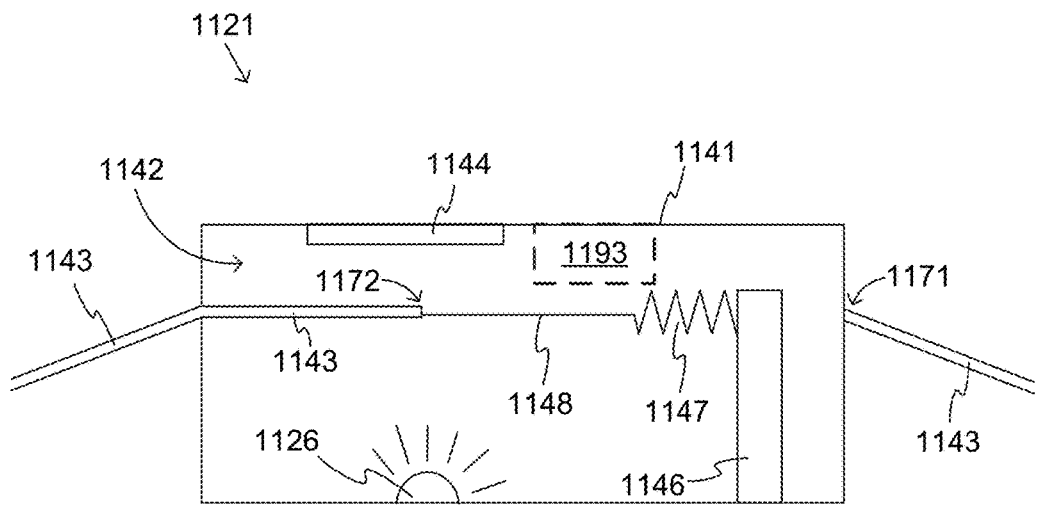
FIG. 11B is a diagram of a detail of a sample embodiment of the sensor module of FIG. 11A.

FIG. 11B is a diagram of a detail of a sample embodiment of the sensor module of FIG. 11A. In this example, elastic band 1143 has two ends 1171, 1172 attached to sensor housing 1141, and sensor housing 1141 is thus pressed towards the chest of the patient by the stretching of elastic band 1143. Sensor housing 1141 has a cavity 1142, and end 1172 reaches within sensor housing 1141. In addition, sensor module 1121 includes a spring 1147 that is coupled to end 1172, for example via a thread 1148. Accordingly, spring 1147 keeps band 1143 stretched against a fixed post 1146. The patient's breathing causes end 1172 to oscillate from left to right and back again.

The oscillation of end 1172 can be detected in a number of ways. In the example of FIG. 11B, a light source 1126 can project light that can be imaged by imager 1144. Imager 1144 can be a pixel array, a small linear array of larger photodetectors, and so on. It helps if band 1143 is wide at end 1172, while thread 1148 is thin, so that end 1172 will cast a shadow, helping imager 1144 detect better. If higher detection sensitivity is desired, end 1172 may be moved lower so that it is closer to light source 1126 than is suggested by the diagram, so that the left-ward move caused by an inhalation of the patient will remove more shadow from imager 1144. Sensor module 1121 may also include a communication device 1193 and other components. A drawback in detecting breathing is that breathing can continue at least briefly after the beginning of cardiac arrest.

In many embodiments, at the time of fitting a WCD system to a patient, it is preferred to have a process for determining which ones of various modules to use, and/or a calibration procedure for them that is specific to the patient. For example, a patient who normally breathes heavily may do well with the sensor module of FIG. 11A, a patient who is white may do well with the sensor module of FIG. 10, and so on.

In yet other embodiments, both the patient's physiological parameter and motion can be monitored in combination. The value of the physiological parameter becomes better informed from the motion profile.

Embodiments of sensor modules are now described that can provide more clarity as to when a particular sensor module is or is not in service. These embodiments may be useful in the event that wirelessly operating sensor modules may be nearby while they are not used at the time, for example being recharged at night while the patient is sleeping, and could still be contributing a signal that could confuse. These embodiments include the provision of an ON/OFF switch, provisions for detecting the environment of the sensor module for inferring whether it is in service or not, etc.

Figure 12A:
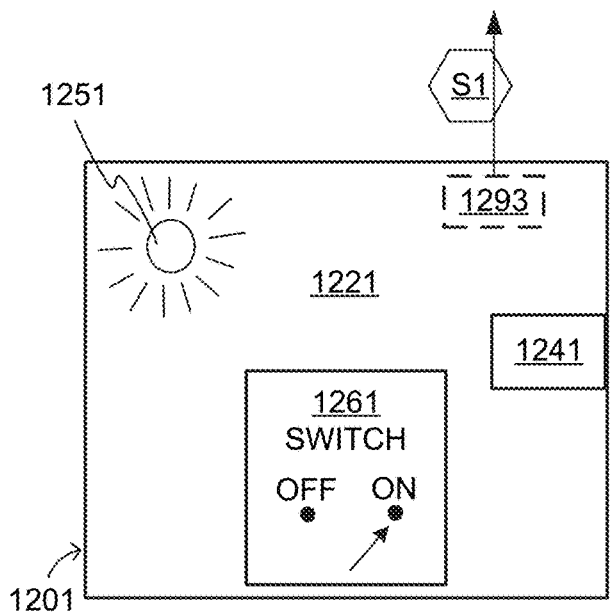
FIGS. 12A and 12B are differential drawings showing how a sensor module made according to embodiments can stop transmitting its signal when it is turned off.
Figure 12B:
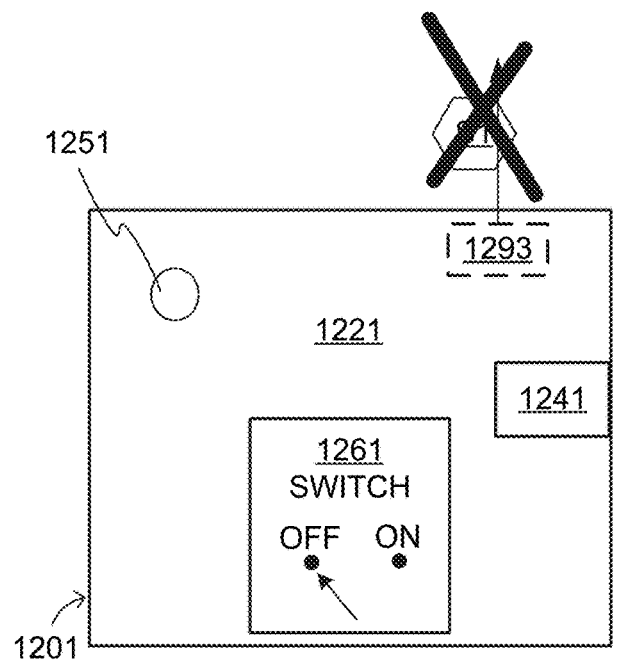

FIGS. 12A and 12B are differential drawings showing how a sensor module made according to embodiments can stop transmitting its signal by becoming definitively turned off. These two drawings can be characterized as differential because they show a single sensor module 1221 in different states, to facilitate comparison based on their similarities and differences.

In particular, FIG. 12A shows a sensor module 1221 that includes a sensor housing 1201. Sensor housing 1201 is configured to be coupled to the patient's body, as mentioned above. Sensor module 1221 also includes a sensor 1241 coupled to sensor housing 1201. Sensor 1241 can be configured to monitor a physiological parameter of the patient, while sensor housing 1201 is coupled to the patient's body, as shown previously, etc. Sensor module 1221 may thus make available a signal S1 that is generated from the monitored parameter. Sensor module 1221 may further include a communication device 1293 configured to communicate signal S1. Sensor module 1221 additionally may include an active visual indicator 1251, which can be made as was described for active visual indicator 951.

Sensor module 1221 further includes an ON/OFF switch 1261. Switch 1261 can be configured to permit a user to place sensor module 1221 in an ON state or an OFF state. The OFF state can be a state where power is turned off, or be a state of low-power dormancy ("sleep"). ON/OFF switch 1261 can be manual, and accessed externally by the patient, as the patient is managing which sensor module to use at the time. ON/OFF switch 1261 can alternately be implemented internally as an electronic state machine, a software flag, and thus be set in the ON state or in the OFF state by another component of the WCD system. For example, in some embodiments, sensor module 1221 may be intentionally lightly bumped against the sensor interface as a way of becoming wirelessly paired with it, and thus being turned ON from a dormant OFF state. Unpairing may be by double-bumping, etc.

In FIG. 12A, ON/OFF switch 1261 indicates that sensor module 1221 is placed in the ON state. Signal S1 is being transmitted. Active visual indicator 1251 is shown as lit, to give confidence to the patient that sensor module 1221 is ON, and signal S1 is being transmitted. In terms of methods, signal S1 is caused to be transmitted, etc.

In such embodiments, sensor module 1221 can be configured to not transmit its signal S1, if sensor module 1221 is placed in the OFF state. For example, as seen in FIG. 12B, ON/OFF switch 1261 is in the OFF position. Signal S1 is not being transmitted, which is why it is shown as crossed-out. Active visual indicator 1251 is accordingly shown as not lit.

In some of the embodiments of FIGS. 12A and 12B, ON/OFF switch 1261 is manual. This may introduce error, if the switch is set inadvertently by the patient moving around, the WCD system bumping into the environment, etc. This source of error may be ameliorated by implementing a protective cover over switch ON/OFF 1261.

In some of the embodiments of FIGS. 12A and 12B, the patient would have to set ON/OFF switch 1261 manually. This may introduce error, if the patient forgets the instructions, forgets to reset ON/OFF switch 1261 upon taking off sensor module 1221, etc. In some embodiments, it is desired to require less such participation by the patient. Additional examples are now described, where the sensor module may detect by itself how it is being used, and control its signal accordingly.

Figure 13A:
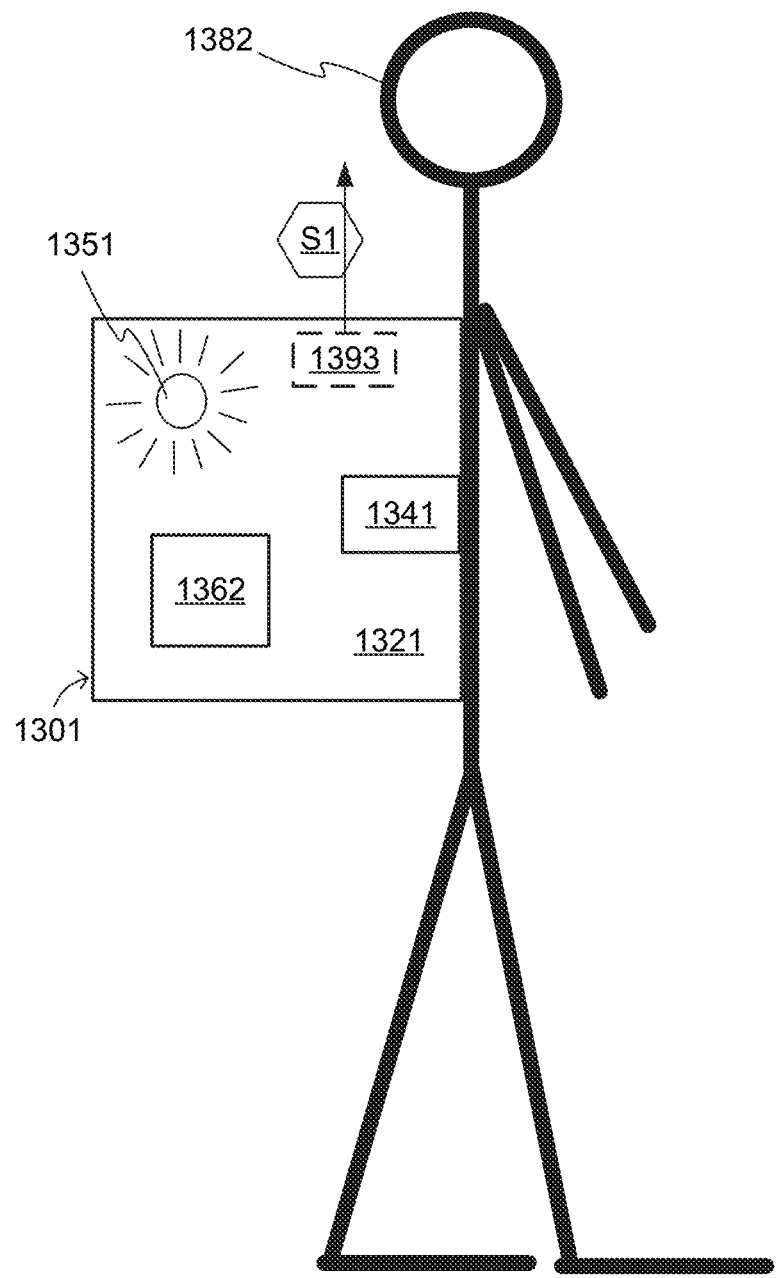
FIGS. 13A and 13B are differential drawings showing how a sensor module made according to embodiments can stop transmitting its signal when it detects that it is no longer monitoring the patient.
Figure 13B:
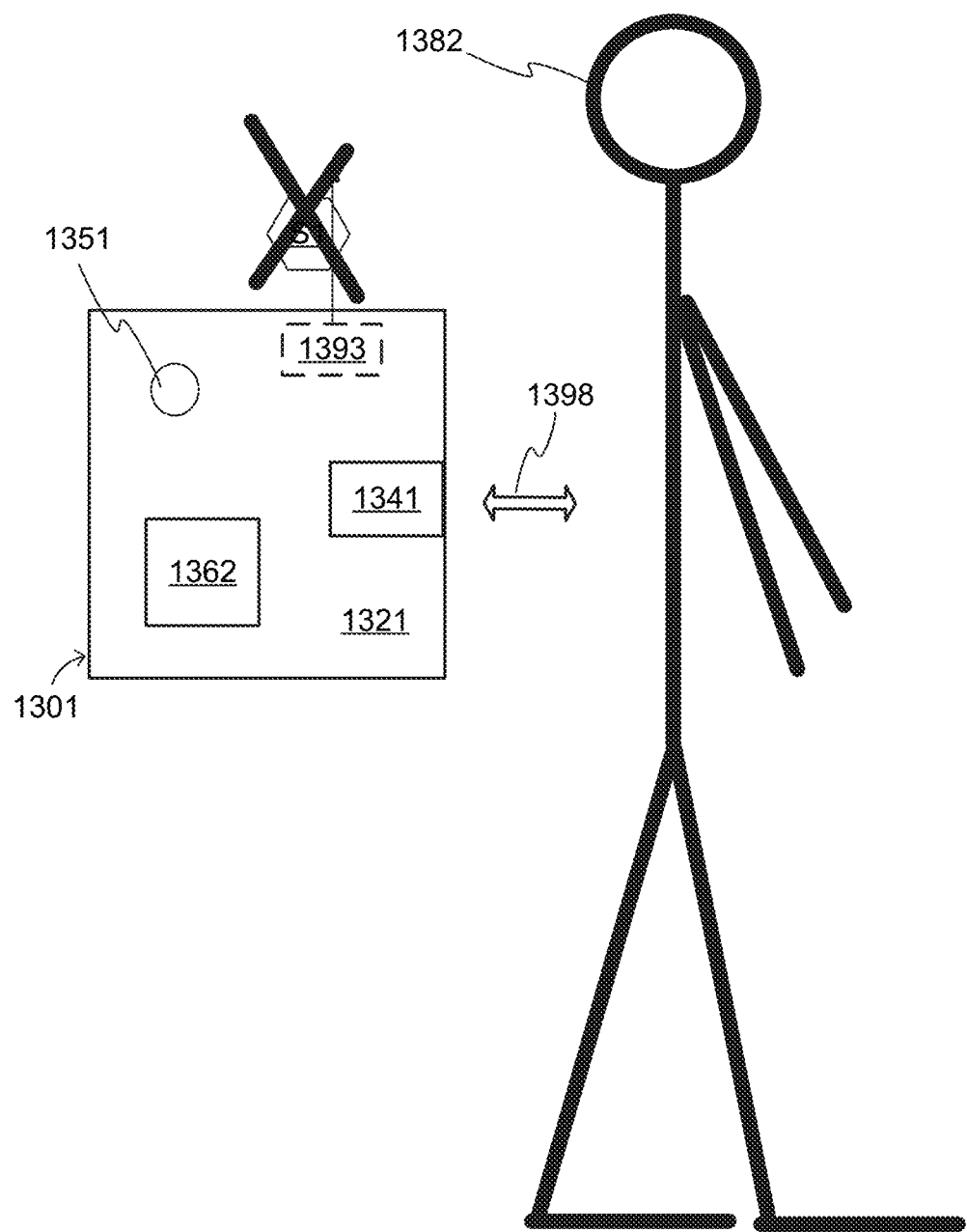

FIGS. 13A and 13B are differential drawings showing how a sensor module 1321 made according to embodiments can stop transmitting its signal, when it detects that it is no longer monitoring the patient.

In particular, FIG. 13A shows sensor module 1321 that includes a sensor housing 1301. Sensor housing 1301 is configured to be coupled to a patient's body, and is indeed so coupled to the body of a patient 1382. Of course, it will be understood that necessities of the drawing artificially require sensor module 1321 to be shown in a space that would have the size of a backpack relative to the size of the body of patient 1382, while in fact sensor module 1321 will typically have a much smaller size.

Sensor module 1321 also includes a sensor 1341 coupled to sensor housing 1301. Sensor 1341 can be configured to monitor a parameter of patient 1382, while sensor housing 1301 is coupled to the body of patient 1382. A first sensing input can thus be generated from the monitored physiological parameter. Sensor module 1321 may thus transmit a signal S1 that communicates the sensing input. Sensor module 1321 may further include a communication device 1393 configured to transmit signal S1. Sensor module 1321 additionally may include an active visual indicator 1351, which can be made as was described for active visual indicator 951.

Sensor module 1321 further includes a status sensor 1362. Status sensor 1362 can be configured to determine whether the sensing input meets a validity criterion. The validity criterion can be about the parameter that is monitored, whether any measurements are valid or not. It is understood that the determination might not always be the correct one, but only an inference that gives acceptable confidence in the right direction.

Status sensor 1362 may be implemented in hardware, software, or combination thereof, and operate in a number of ways. For example, the validity criterion might not be met depending on whether or not the values of the parameter monitored by sensor 1341 are consistent with values expected for patient 1382 to be a) doing well, b) experiencing an SCA, or c) wearing or no longer wearing sensor module 1321. For example, it can be determined that the sensing input does not meet the validity criterion if the sensing input has a value that is larger or smaller than a validity threshold for the physiological parameter.

In embodiments, status sensor 1362 may use patient status data additional to or different from what is learned by sensor 1341 monitoring the patient parameter. In such embodiments, status sensor 1362 may include one or more of a temperature sensor, a time-keeping mechanism, a motion sensor, a light sensor, a capacitance sensor, etc.

The temperature sensor may exploit the fact that the patient's temperature is normally within a narrow range. It can exploit this by being placed close to the patient's skin, and in a position relatively thermally shielded from the surroundings. Then, if the temperature changes to become similar to, say, room temperature, it could be inferred that sensor module 1321 may have been removed from the patient's body.

The time-keeping mechanism may track the time of day, and create expectations as to what other patient status data might be, such as motion and ambient light. In turn, such patient status data might be checked against an output of a motion sensor and a light sensor that tracks an amount of ambient light. A capacitance sensor may help detect any sudden changes in capacitance, such as might happen when sensor module 1321 is becoming attached to the body or being taken off. All this data can help improve the determination of whether the patient is wearing or no longer wearing the sensor module and, if wearing it, whether the patient is doing well or not.

In FIG. 13A, sensor module 1321 is coupled to the body of patient 1382, by virtue of sensor housing 1301 being coupled to the body of a patient 1382. Signal S1 is being transmitted. Active visual indicator 1351, which could be an LED, is shown as lit. This may give confidence to patient 1382 that sensor module 1321 is ON, and signal S1 is being transmitted.

In such embodiments, sensor module 1321 can be configured to not transmit its signal S1, if it is determined that the first parameter does not meet the validity criterion. For example, as seen in FIG. 13B, there is a physical separation 1398 between patient 1382 and sensor module 1321. In other words, sensor module 1321 is no longer coupled to the body of patient 1382—patient 1382 has removed sensor module 1321. The validity criterion is determined to not be met. Accordingly, signal S1 is not being transmitted, which is why it is shown as crossed out. Active visual indicator 1351 is not lit.

In many of the embodiments of FIGS. 13A and 13B, the detection was made based on interpreting what was sensed by sensor 1341. In other embodiments, a sensor module may detect whether it is being recharged, and the status sensor is adapted accordingly.

Figure 14A:
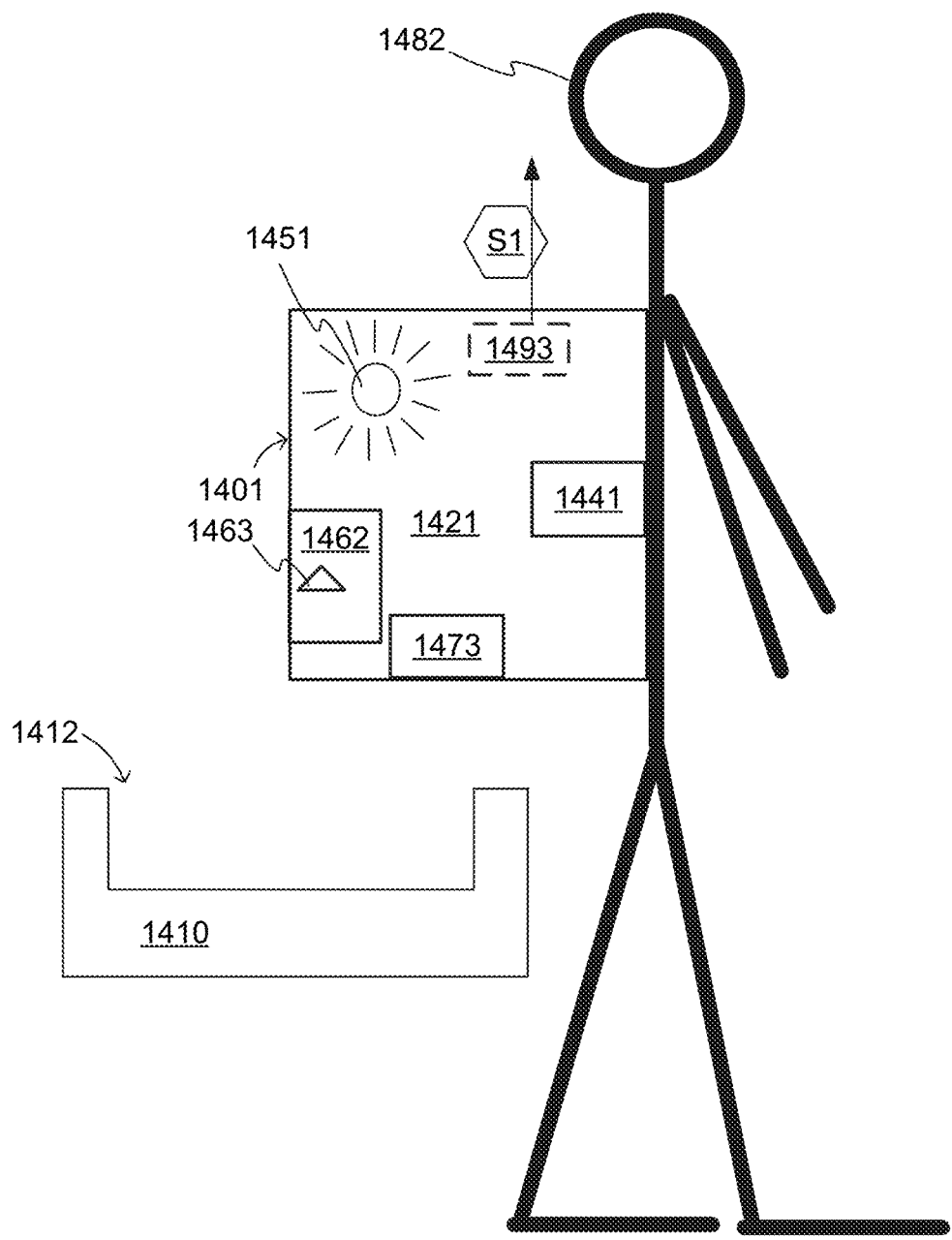
FIGS. 14A and 14B are differential drawings showing how a sensor module made according to embodiments can stop transmitting its signal while being charged.
Figure 14B:
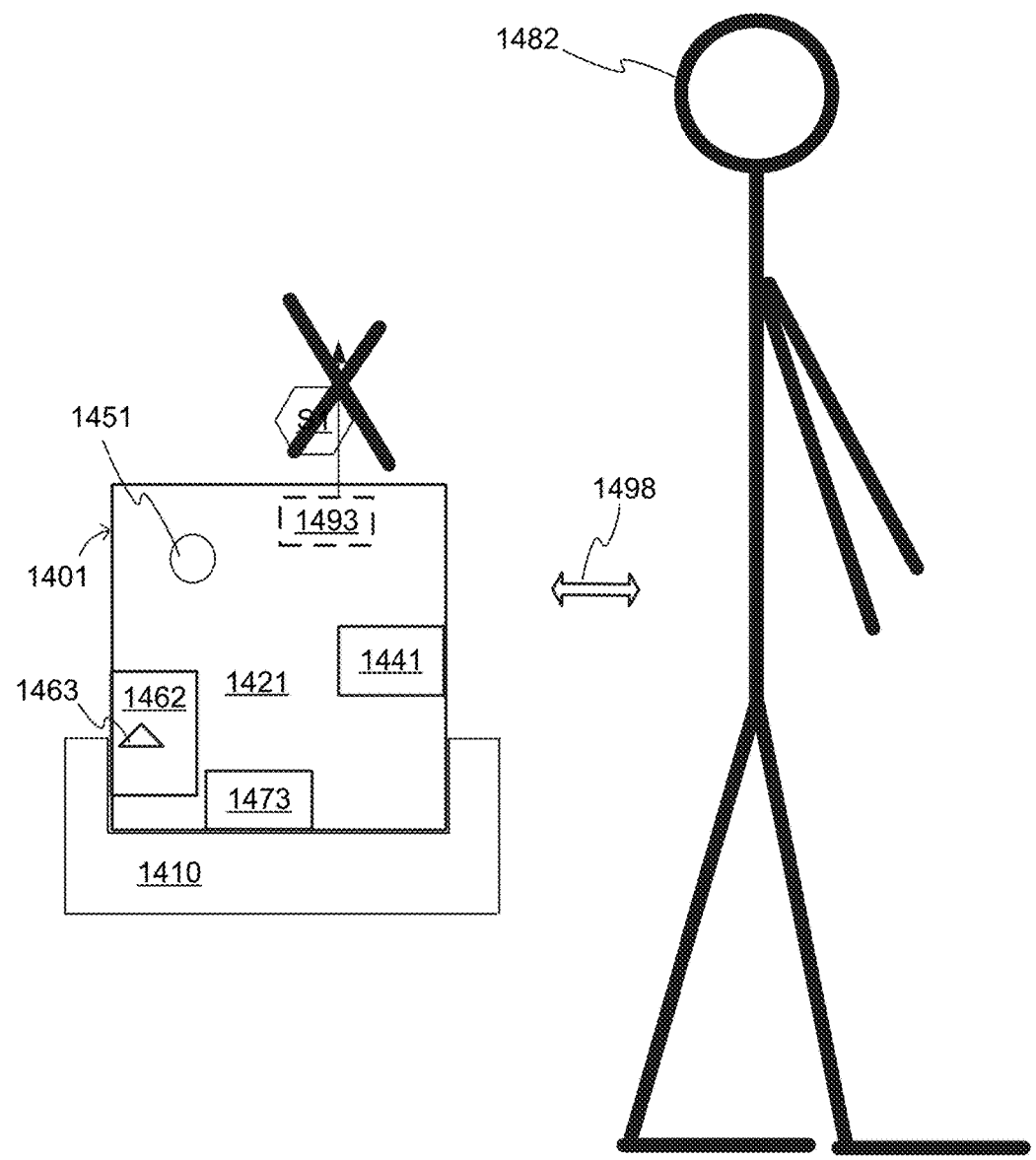

FIGS. 14A and 14B are differential drawings showing how a sensor module made according to embodiments can stop transmitting its signal while being charged. The inference is that, while being charged, the sensor module is necessarily not monitoring the patient.

In particular, FIG. 14A shows a sensor module 1421 that includes a sensor housing 1401. Sensor housing 1401 is configured to be coupled to a patient's body, and is indeed so coupled to the body of a patient 1482. Sensor module 1421 also includes a sensor 1441 coupled to sensor housing 1401. Sensor 1441 can be configured to monitor a parameter of patient 1482, while sensor housing 1401 is coupled to the body of patient 1482. Sensor module 1421 may thus transmit a signal S1. Sensor module 1421 may further include a communication device 1493. Sensor module 1421 additionally may include an active visual indicator 1451, which can be made as was described for active visual indicator 951.

In FIG. 14A, sensor module 1421 is coupled to the body of patient 1482, by virtue of sensor housing 1401 being coupled to the body of patient 1482. Signal S1 is being transmitted. Active visual indicator 1451 is lit, to give confidence to patient 1482 that sensor module 1421 is ON, and signal S1 is being transmitted.

Sensor module 1421 further includes a rechargeable battery 1473 within sensor housing 1401. Rechargeable battery 1473 can be configured to be charged via a charging station 1410, which may have a receptacle 1412. Charging station 1410 may or may not be part of the WCD system. Rechargeable battery 1473 can be configured to be charged while sensor housing 1401 is placed in receptacle 1412. A charging visual indicator (not shown) on sensor module 1421 can be configured to indicate that rechargeable battery 1473 is indeed being charged, while sensor housing 1401 is placed in charging station 1410.

Sensor module 1421 moreover includes a status sensor 1462. Status sensor 1462 may include a charger detector 1463 that is configured to detect whether or not rechargeable battery 1473 is being charged by charging station 1410. In such embodiments, the validity criterion is not met if it is detected that rechargeable battery 1473 is being charged by charging station 1410. Charger detector 1463 may be implemented in different ways.

In some embodiments, rechargeable battery 1473 is configured to be charged by sensor housing 1401 being placed in charging station 1410. Charger detector 1463 can be configured to detect whether or not sensor housing 1401 is placed in charging station 1410. For example, charger detector 1463 can include a mechanical pin that becomes pressed by a side wall of receptacle 1412.

In some embodiments, charger detector 1463 is configured to detect electrically whether or not rechargeable battery 1473 is being charged. For example, charger detector 1463 can include a component that detects current flowing into rechargeable battery 1473, etc.

In some embodiments, the WCD system further comprises the charging station.

In such embodiments, sensor module 1421 can be configured to not transmit its signal S1, while its sensor housing 1401 is being charged by charging station 1410. For example, as seen in FIG. 14B, sensor housing 1401 has been placed in charging station 1410, battery 1473 is being recharged, and there is a physical separation 1498 between patient 1482 and sensor module 1421. In other words, sensor module 1421 is no longer coupled to the body of patient 1482, because sensor module 1421 is being charged. Accordingly, signal S1 is not being transmitted, which is why it is shown crossed out. Active visual indicator 1451 is not lit.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A wearable cardioverter defibrillator (WCD) system, comprising:
   a support structure that may be worn by a patient;
   a processor coupled to the support structure;
   a discharge circuit configured to discharge a stored electrical charge through a body of the patient, the discharge circuit in communication with the processor;
   at least two sensors in communication with the processor, the at least two sensors including at least a physiological sensor configured and positioned to detect a physiological parameter of the patient and a motion sensor configured and positioned to detect that the WCD is in motion;
   the processor configured to:
      determine from the physiological parameter whether or not a first shock criterion is met;
      in response to the first shock criterion being met, determine, from an output of the motion sensor, whether the WCD is in motion;
      in response to motion being detected, determine a second shock criterion is not satisfied; and
      maintain an inactivate state of the discharge circuit.

2. The WCD system of claim 1, wherein the second shock criterion is a lack of sufficient movement of the patient.

3. The WCD system of claim 1, wherein the motion sensor comprises an accelerometer and the accelerometer is coupled to the support structure.

4. The WCD system of claim 1 wherein the motion sensor comprises an accelerometer and the accelerometer is coupled to the body of the patient and is in wireless communication with the processor.

5. The WCD system of claim 1, wherein the processor is further configured to:
   receive an output from a third sensor remote from the WCD system;
   analyze the output from the third sensor; and
   activate the discharge circuit when the analyzed output of the third sensor satisfies the second shock criterion.

6. The WCD system of claim 1, wherein the processor is further configured to:
   receive outputs from a multiple sensors separate from the WCD system;
   analyze the outputs from the multiple sensors; and
   compare the analyzed outputs to the second shock criterion.

7. The WCD system of claim 1, wherein the motion sensor is one of an accelerometer and a pressure sensor.

8. The WCD system of claim 1, wherein the processor is further configured to generate a polling signal to the motion sensor at a predetermined time interval.

9. The WCD system of claim 8, wherein the predetermined time interval is between 10 seconds and 60 seconds.

10. The WCD system of claim 8, wherein the processor is still further configured to cause the motion sensor to enter a rapid polling process.

11. The WCD system of claim 10, wherein the rapid polling process prompts the processor to continuously poll the motion sensor for a predetermined length of time.

12. The WCD system of claim 11; wherein, when a detected motion does not satisfy the second shock criterion during the predetermined length of time, the processor is configured to activate the discharge circuit.

13. The WCD system of claim 11, wherein, when a detected motion does not satisfy the second shock criterion during the predetermined length of time, the processor is configured to activate an alarm of an impending electrical charge.

14. The WCD system of claim 1, wherein the processor further generates a reassurance code from the determination of the second shock criterion, and wherein the reassurance code inhibits the discharge circuit from emitting the stored electrical charge.

15. The WCD system of claim 1, further comprising:
   an active visual indicator coupled to each of the at least two sensors, wherein the active visual indicator is configured to indicate each the at least two sensors is transmitting data to the processor.

16. A wearable cardioverter defibrillator system, comprising:
   a support structure for wearing by a patient;
   a defibrillator housing coupled to the support structure;
   a discharge circuit in communication with the defibrillator housing; the discharge circuit configured to discharge a stored electrical charge through a body of the patient,
   a processor within the defibrillator housing, the processor in communication with the discharge circuit;
   at least one physiological sensor in communication with the processor, the physiological sensor positioned to ECG parameter of the patient; and
   at least one motion sensor in communication with the processor, the motion sensor positioned to detect movement of the patient;
   the processor configured to:
      determine from the ECG parameter whether or not a first shock criterion is met;
      receive a second parameter from the at least one motion sensor;
      determine, from the received signal, whether the patient is in motion; and
      activate the discharge circuit to emit the stored electrical charge to the patient when the motion does not satisfy a second shock criterion.

17. The WCD system of claim 16, wherein the processor is further configured to:
   generate an alarm to be dispatched to the patient when the second shock criterion is not satisfied;
   determine when a response to the generated alarm is received; and
   deactivate the discharge circuit when the response to the generated alarm is received.

18. The WCD system of claim 16, wherein the processor is further configured to:
   receive data from at least one sensor external to the WCD system;
   analyze data from the at least one sensor; and
   compare the analyzed data to the first and second shock criterion.

19. The WCD system of claim 16, wherein the processor is further configured to:
   receive data from multiple sensors external to the WCD system; and determine from the multiple sensors when a secondary shock criterion is met.

20. A wearable cardioverter defibrillator system, comprising:
- a support structure for wearing by a patient;
- one or more electrodes for delivering a charge to the patient, while the patient is wearing the support structure;
- a discharge circuit coupled to the electrodes, the discharge circuit configured to store an electrical charge;
- a processor for activating the discharge circuit, the processor in communication with the discharge circuit;
- at least one physiological sensor module in communication with the processor, the at least one physiological sensor module configured to monitor a physiological parameter of the patient while the patient wears the support structure and to transmit a first signal that communicates the physiological parameter; and
- at least one motion sensor module in communication with the processor, the at least one motion sensor module configured to monitor a motion parameter of the patient while the patient wears the support structure and to transmit a second signal that communicates the motion parameter.

21. The WCD system of claim 20, in which the at least one motion sensor module encodes a reassurance code generated from a value of the second signal.

22. The WCD system of claim 21, wherein the at least one motion sensor module is configured to communicate the reassurance code to the processor and the processor inhibits signals for shocking when the reassurance code is received.

23. The WCD system of claim 20, wherein the at least one motion sensor module further includes:
- a sensor housing configured to be worn by the patient; and
- a sensor coupled to the sensor housing and configured to monitor the motion parameter while the sensor housing is worn by the patient.

24. The WCD system of claim 20, in which the at least one motion sensor module includes a communication device configured to transmit the second signal to the processor.

25. The WCD system of claim 24, in which
the communication device is configured to transmit the second signal wirelessly.

26. The WCD system of claim 24, in which
the communication device is configured to transmit the second signal periodically within one hour.

27. The WCD system of claim 24, in which
the at least one motion sensor module is configured to receive a polling signal; and
the communication device is configured to transmit the second signal responsive to the at least one motion sensor receiving the polling signal.

28. The WCD system of claim 27, wherein the at least one motion sensor module is configured to generate the second signal when the first signal transmits a shock code.

29. The WCD system of claim 28, in which
the second signal encodes a reassurance code generated from a value of the motion parameter.

30. The WCD system of claim 29, wherein the processor inhibits signals for shocking when the reassurance code is received from the at least one motion sensor module.

* * * * *

UNITED STATES PATENT AND TRADEMARK OFFICE
CERTIFICATE OF CORRECTION

PATENT NO. : 10,478,631 B2
APPLICATION NO. : 15/905575
DATED : November 19, 2019
INVENTOR(S) : F. W. Chapman et al.

Page 1 of 1

It is certified that error appears in the above-identified patent and that said Letters Patent is hereby corrected as shown below:

In the Claims

| Column | Line | |
|---|---|---|
| 24 | 34-35 | "ECG parameter" should read --monitor an ECG |
| (Claim 16, | Lines 11-12) | parameter-- Insert after "to" on Line 34 and before "of" on Line 35 |

Signed and Sealed this
Twenty-first Day of April, 2020

Andrei Iancu
*Director of the United States Patent and Trademark Office*